US009945777B2

United States Patent
Gillet (10) Patent No.: US 9,945,777 B2
(45) Date of Patent: Apr. 17, 2018

(54) MULTI-SPECTRAL IMAGING USING LONGITUDINAL CHROMATIC ABERRATIONS

(71) Applicant: Hand Held Products, Inc., Fort Mill, SC (US)

(72) Inventor: Alain Gillet, Galan (FR)

(73) Assignee: Hand Held Products, Inc., Fort Mill, SC (US)

( * ) Notice: Subject to any disclaimer, the term of this patent is extended or adjusted under 35 U.S.C. 154(b) by 0 days.

(21) Appl. No.: 14/995,613

(22) Filed: Jan. 14, 2016

(65) Prior Publication Data

US 2017/0205341 A1    Jul. 20, 2017

(51) Int. Cl.

| | | |
|---|---|---|
| *G01N 21/31* | (2006.01) | |
| *G01N 21/359* | (2014.01) | |
| *G01N 21/33* | (2006.01) | |
| *G02B 27/00* | (2006.01) | |
| *G02B 3/14* | (2006.01) | |
| *G02B 26/00* | (2006.01) | |
| *G06K 7/14* | (2006.01) | |

(52) U.S. Cl.
CPC ........... *G01N 21/359* (2013.01); *G01N 21/31* (2013.01); *G01N 21/33* (2013.01); *G02B 3/14* (2013.01); *G02B 26/005* (2013.01); *G02B 27/0025* (2013.01); *G06K 7/1408* (2013.01)

(58) Field of Classification Search
CPC ...... G01N 21/359; G01N 21/31; G01N 21/33; G02B 3/14
See application file for complete search history.

(56) References Cited

U.S. PATENT DOCUMENTS

| | | | |
|---|---|---|---|
| 5,359,185 A | 10/1994 | Hanson | |
| 5,479,258 A | 12/1995 | Hinnrichs | |
| 6,172,745 B1 | 1/2001 | Voser et al. | |
| 6,765,617 B1 * | 7/2004 | Tangen | H01L 27/14627 |
| | | | 348/340 |
| 6,832,725 B2 | 12/2004 | Gardiner et al. | |
| 7,128,266 B2 | 10/2006 | Zhu et al. | |
| 7,159,783 B2 | 1/2007 | Walczyk et al. | |

(Continued)

FOREIGN PATENT DOCUMENTS

| | | |
|---|---|---|
| EP | 2246802 A2 | 11/2010 |
| EP | 2789999 A1 | 10/2014 |

(Continued)

OTHER PUBLICATIONS

U.S. Appl. No. 14/715,916 for Evaluating Image Values filed May 19, 2015 (Ackley); 60 pages.

(Continued)

*Primary Examiner* — Marcus Taningco
(74) *Attorney, Agent, or Firm* — Additon, Higgins & Pendleton, P.A.

(57) ABSTRACT

Systems and methods for imaging a target object are provided. In one example, an imaging device comprises an objective lens having symmetry around an optical axis. The objective lens is configured to disperse images of a target object in longitudinal chromatic aberrations along the optical axis. The imaging device further includes a sensor configured to obtain multiple images of the target object. Each image corresponds to a specific wavelength within a predetermined spectrum.

18 Claims, 3 Drawing Sheets

(56) References Cited

U.S. PATENT DOCUMENTS

| | | |
|---|---|---|
| 7,413,127 B2 | 8/2008 | Ehrhart et al. |
| 7,726,575 B2 | 6/2010 | Wang et al. |
| 8,126,205 B2 * | 2/2012 | Levenson ............... G01N 21/23 382/103 |
| 8,294,969 B2 | 10/2012 | Plesko |
| 8,317,105 B2 | 11/2012 | Kotlarsky et al. |
| 8,322,622 B2 | 12/2012 | Liu |
| 8,366,005 B2 | 2/2013 | Kotlarsky et al. |
| 8,371,507 B2 | 2/2013 | Haggerty et al. |
| 8,376,233 B2 | 2/2013 | Van Horn et al. |
| 8,381,979 B2 | 2/2013 | Franz |
| 8,390,909 B2 | 3/2013 | Plesko |
| 8,408,464 B2 | 4/2013 | Zhu et al. |
| 8,408,468 B2 | 4/2013 | Horn et al. |
| 8,408,469 B2 | 4/2013 | Good |
| 8,424,768 B2 | 4/2013 | Rueblinger et al. |
| 8,448,863 B2 | 5/2013 | Xian et al. |
| 8,457,013 B2 | 6/2013 | Essinger et al. |
| 8,459,557 B2 | 6/2013 | Havens et al. |
| 8,469,272 B2 | 6/2013 | Kearney |
| 8,474,712 B2 | 7/2013 | Kearney et al. |
| 8,479,992 B2 | 7/2013 | Kotlarsky et al. |
| 8,490,877 B2 | 7/2013 | Kearney |
| 8,517,271 B2 | 8/2013 | Kotlarsky et al. |
| 8,523,076 B2 | 9/2013 | Good |
| 8,528,818 B2 | 9/2013 | Ehrhart et al. |
| 8,544,737 B2 | 10/2013 | Gomez et al. |
| 8,548,420 B2 | 10/2013 | Grunow et al. |
| 8,550,335 B2 | 10/2013 | Samek et al. |
| 8,550,354 B2 | 10/2013 | Gannon et al. |
| 8,550,357 B2 | 10/2013 | Kearney |
| 8,556,174 B2 | 10/2013 | Kosecki et al. |
| 8,556,176 B2 | 10/2013 | Van Horn et al. |
| 8,556,177 B2 | 10/2013 | Hussey et al. |
| 8,559,767 B2 | 10/2013 | Barber et al. |
| 8,561,895 B2 | 10/2013 | Gomez et al. |
| 8,561,903 B2 | 10/2013 | Sauerwein |
| 8,561,905 B2 | 10/2013 | Edmonds et al. |
| 8,565,107 B2 | 10/2013 | Pease et al. |
| 8,571,307 B2 | 10/2013 | Li et al. |
| 8,579,200 B2 | 11/2013 | Samek et al. |
| 8,583,924 B2 | 11/2013 | Caballero et al. |
| 8,584,945 B2 | 11/2013 | Wang et al. |
| 8,587,595 B2 | 11/2013 | Wang |
| 8,587,697 B2 | 11/2013 | Hussey et al. |
| 8,588,869 B2 | 11/2013 | Sauerwein et al. |
| 8,590,789 B2 | 11/2013 | Nahill et al. |
| 8,596,539 B2 | 12/2013 | Havens et al. |
| 8,596,542 B2 | 12/2013 | Havens et al. |
| 8,596,543 B2 | 12/2013 | Havens et al. |
| 8,599,271 B2 | 12/2013 | Havens et al. |
| 8,599,957 B2 | 12/2013 | Peake et al. |
| 8,600,158 B2 | 12/2013 | Li et al. |
| 8,600,167 B2 | 12/2013 | Showering |
| 8,602,309 B2 | 12/2013 | Longacre et al. |
| 8,608,053 B2 | 12/2013 | Meier et al. |
| 8,608,071 B2 | 12/2013 | Liu et al. |
| 8,611,309 B2 | 12/2013 | Wang et al. |
| 8,615,487 B2 | 12/2013 | Gomez et al. |
| 8,621,123 B2 | 12/2013 | Caballero |
| 8,622,303 B2 | 1/2014 | Meier et al. |
| 8,628,013 B2 | 1/2014 | Ding |
| 8,628,015 B2 | 1/2014 | Wang et al. |
| 8,628,016 B2 | 1/2014 | Winegar |
| 8,629,926 B2 | 1/2014 | Wang |
| 8,630,491 B2 | 1/2014 | Longacre et al. |
| 8,635,309 B2 | 1/2014 | Berthiaume et al. |
| 8,636,200 B2 | 1/2014 | Kearney |
| 8,636,212 B2 | 1/2014 | Nahill et al. |
| 8,636,215 B2 | 1/2014 | Ding et al. |
| 8,636,224 B2 | 1/2014 | Wang |
| 8,638,806 B2 | 1/2014 | Wang et al. |
| 8,640,958 B2 | 2/2014 | Lu et al. |
| 8,640,960 B2 | 2/2014 | Wang et al. |
| 8,643,717 B2 | 2/2014 | Li et al. |
| 8,646,692 B2 | 2/2014 | Meier et al. |
| 8,646,694 B2 | 2/2014 | Wang et al. |
| 8,657,200 B2 | 2/2014 | Ren et al. |
| 8,659,397 B2 | 2/2014 | Vargo et al. |
| 8,668,149 B2 | 3/2014 | Good |
| 8,678,285 B2 | 3/2014 | Kearney |
| 8,678,286 B2 | 3/2014 | Smith et al. |
| 8,682,077 B1 | 3/2014 | Longacre |
| D702,237 S | 4/2014 | Oberpriller et al. |
| 8,687,282 B2 | 4/2014 | Feng et al. |
| 8,692,927 B2 | 4/2014 | Pease et al. |
| 8,695,880 B2 | 4/2014 | Bremer et al. |
| 8,698,949 B2 | 4/2014 | Grunow et al. |
| 8,702,000 B2 | 4/2014 | Barber et al. |
| 8,717,494 B2 | 5/2014 | Gannon |
| 8,720,783 B2 | 5/2014 | Biss et al. |
| 8,723,804 B2 | 5/2014 | Fletcher et al. |
| 8,723,904 B2 | 5/2014 | Marty et al. |
| 8,727,223 B2 | 5/2014 | Wang |
| 8,740,082 B2 | 6/2014 | Wilz |
| 8,740,085 B2 | 6/2014 | Furlong et al. |
| 8,746,563 B2 | 6/2014 | Hennick et al. |
| 8,750,445 B2 | 6/2014 | Peake et al. |
| 8,752,766 B2 | 6/2014 | Xian et al. |
| 8,756,059 B2 | 6/2014 | Braho et al. |
| 8,757,495 B2 | 6/2014 | Qu et al. |
| 8,760,563 B2 | 6/2014 | Koziol et al. |
| 8,763,909 B2 | 7/2014 | Reed et al. |
| 8,777,108 B2 | 7/2014 | Coyle |
| 8,777,109 B2 | 7/2014 | Oberpriller et al. |
| 8,779,898 B2 | 7/2014 | Havens et al. |
| 8,781,520 B2 | 7/2014 | Payne et al. |
| 8,783,573 B2 | 7/2014 | Havens et al. |
| 8,789,757 B2 | 7/2014 | Barten |
| 8,789,758 B2 | 7/2014 | Hawley et al. |
| 8,789,759 B2 | 7/2014 | Xian et al. |
| 8,794,520 B2 | 8/2014 | Wang et al. |
| 8,794,522 B2 | 8/2014 | Ehrhart |
| 8,794,525 B2 | 8/2014 | Amundsen et al. |
| 8,794,526 B2 | 8/2014 | Wang et al. |
| 8,798,367 B2 | 8/2014 | Ellis |
| 8,807,431 B2 | 8/2014 | Wang et al. |
| 8,807,432 B2 | 8/2014 | Van Horn et al. |
| 8,817,242 B2 | 8/2014 | Bloss et al. |
| 8,820,630 B2 | 9/2014 | Qu et al. |
| 8,822,848 B2 | 9/2014 | Meagher |
| 8,824,692 B2 | 9/2014 | Sheerin et al. |
| 8,824,696 B2 | 9/2014 | Braho |
| 8,842,849 B2 | 9/2014 | Wahl et al. |
| 8,844,822 B2 | 9/2014 | Kotlarsky et al. |
| 8,844,823 B2 | 9/2014 | Fritz et al. |
| 8,849,019 B2 | 9/2014 | Li et al. |
| D716,285 S | 10/2014 | Chaney et al. |
| 8,851,383 B2 | 10/2014 | Yeakley et al. |
| 8,854,633 B2 | 10/2014 | Laffargue et al. |
| 8,866,963 B2 | 10/2014 | Grunow et al. |
| 8,868,421 B2 | 10/2014 | Braho et al. |
| 8,868,519 B2 | 10/2014 | Maloy et al. |
| 8,868,802 B2 | 10/2014 | Barten |
| 8,868,803 B2 | 10/2014 | Caballero |
| 8,870,074 B1 | 10/2014 | Gannon |
| 8,879,639 B2 | 11/2014 | Sauerwein |
| 8,880,426 B2 | 11/2014 | Smith |
| 8,881,983 B2 | 11/2014 | Havens et al. |
| 8,881,987 B2 | 11/2014 | Wang |
| 8,903,172 B2 | 12/2014 | Smith |
| 8,908,995 B2 | 12/2014 | Benos et al. |
| 8,910,870 B2 | 12/2014 | Li et al. |
| 8,910,875 B2 | 12/2014 | Ren et al. |
| 8,914,290 B2 | 12/2014 | Hendrickson et al. |
| 8,914,788 B2 | 12/2014 | Pettinelli et al. |
| 8,915,439 B2 | 12/2014 | Feng et al. |
| 8,915,444 B2 | 12/2014 | Havens et al. |
| 8,916,789 B2 | 12/2014 | Woodburn |
| 8,918,250 B2 | 12/2014 | Hollifield |
| 8,918,564 B2 | 12/2014 | Caballero |
| 8,925,818 B2 | 1/2015 | Kosecki et al. |
| 8,939,374 B2 | 1/2015 | Jovanovski et al. |
| 8,942,480 B2 | 1/2015 | Ellis |

(56) References Cited

U.S. PATENT DOCUMENTS

| | | |
|---|---|---|
| 8,944,313 B2 | 2/2015 | Williams et al. |
| 8,944,327 B2 | 2/2015 | Meier et al. |
| 8,944,332 B2 | 2/2015 | Harding et al. |
| 8,950,678 B2 | 2/2015 | Germaine et al. |
| D723,560 S | 3/2015 | Zhou et al. |
| 8,967,468 B2 | 3/2015 | Gomez et al. |
| 8,971,346 B2 | 3/2015 | Sevier |
| 8,976,030 B2 | 3/2015 | Cunningham et al. |
| 8,976,368 B2 | 3/2015 | Akel et al. |
| 8,978,981 B2 | 3/2015 | Guan |
| 8,978,983 B2 | 3/2015 | Bremer et al. |
| 8,978,984 B2 | 3/2015 | Hennick et al. |
| 8,985,456 B2 | 3/2015 | Zhu et al. |
| 8,985,457 B2 | 3/2015 | Soule et al. |
| 8,985,459 B2 | 3/2015 | Kearney et al. |
| 8,985,461 B2 | 3/2015 | Gelay et al. |
| 8,988,578 B2 | 3/2015 | Showering |
| 8,988,590 B2 | 3/2015 | Gillet et al. |
| 8,991,704 B2 | 3/2015 | Hopper et al. |
| 8,996,194 B2 | 3/2015 | Davis et al. |
| 8,996,384 B2 | 3/2015 | Funyak et al. |
| 8,998,091 B2 | 4/2015 | Edmonds et al. |
| 9,002,641 B2 | 4/2015 | Showering |
| 9,007,368 B2 | 4/2015 | Laffargue et al. |
| 9,010,641 B2 | 4/2015 | Qu et al. |
| 9,015,513 B2 | 4/2015 | Murawski et al. |
| 9,016,576 B2 | 4/2015 | Brady et al. |
| D730,357 S | 5/2015 | Fitch et al. |
| 9,022,288 B2 | 5/2015 | Nahill et al. |
| 9,030,964 B2 | 5/2015 | Essinger et al. |
| 9,033,240 B2 | 5/2015 | Smith et al. |
| 9,033,242 B2 | 5/2015 | Gillet et al. |
| 9,036,054 B2 | 5/2015 | Koziol et al. |
| 9,037,344 B2 | 5/2015 | Chamberlin |
| 9,038,911 B2 | 5/2015 | Xian et al. |
| 9,038,915 B2 | 5/2015 | Smith |
| D730,901 S | 6/2015 | Oberpriller et al. |
| D730,902 S | 6/2015 | Fitch et al. |
| D733,112 S | 6/2015 | Chaney et al. |
| 9,047,098 B2 | 6/2015 | Barten |
| 9,047,359 B2 | 6/2015 | Caballero et al. |
| 9,047,420 B2 | 6/2015 | Caballero |
| 9,047,525 B2 | 6/2015 | Barber |
| 9,047,531 B2 | 6/2015 | Showering et al. |
| 9,049,640 B2 | 6/2015 | Wang et al. |
| 9,053,055 B2 | 6/2015 | Caballero |
| 9,053,378 B1 | 6/2015 | Hou et al. |
| 9,053,380 B2 | 6/2015 | Xian et al. |
| 9,057,641 B2 | 6/2015 | Amundsen et al. |
| 9,058,526 B2 | 6/2015 | Powilleit |
| 9,064,165 B2 | 6/2015 | Havens et al. |
| 9,064,167 B2 | 6/2015 | Xian et al. |
| 9,064,168 B2 | 6/2015 | Todeschini et al. |
| 9,064,254 B2 | 6/2015 | Todeschini et al. |
| 9,066,032 B2 | 6/2015 | Wang |
| 9,070,032 B2 | 6/2015 | Corcoran |
| D734,339 S | 7/2015 | Zhou et al. |
| D734,751 S | 7/2015 | Oberpriller et al. |
| 9,082,023 B2 | 7/2015 | Feng et al. |
| 9,224,022 B2 | 12/2015 | Ackley et al. |
| 9,224,027 B2 | 12/2015 | Van Horn et al. |
| D747,321 S | 1/2016 | London et al. |
| 9,230,140 B1 | 1/2016 | Ackley |
| 9,250,712 B1 | 2/2016 | Todeschini |
| 9,258,033 B2 | 2/2016 | Showering |
| 9,262,633 B1 | 2/2016 | Todeschini et al. |
| 9,310,609 B2 | 4/2016 | Rueblinger et al. |
| D757,009 S | 5/2016 | Oberpriller et al. |
| 9,342,724 B2 | 5/2016 | McCloskey |
| 9,375,945 B1 | 6/2016 | Bowles |
| D760,719 S | 7/2016 | Zhou et al. |
| 9,390,596 B1 | 7/2016 | Todeschini |
| D762,604 S | 8/2016 | Fitch et al. |
| D762,647 S | 8/2016 | Fitch et al. |
| 9,412,242 B2 | 8/2016 | Van Horn et al. |
| D766,244 S | 9/2016 | Zhou et al. |
| 9,443,123 B2 | 9/2016 | Hejl |
| 9,443,222 B2 | 9/2016 | Singel et al. |
| 9,478,113 B2 | 10/2016 | Xie et al. |
| 2003/0098350 A1* | 5/2003 | Liou .................. G06K 7/10881 235/462.25 |
| 2007/0063048 A1 | 3/2007 | Havens et al. |
| 2009/0134221 A1 | 5/2009 | Zhu et al. |
| 2010/0177076 A1 | 7/2010 | Essinger et al. |
| 2010/0177080 A1 | 7/2010 | Essinger et al. |
| 2010/0177707 A1 | 7/2010 | Essinger et al. |
| 2010/0177749 A1 | 7/2010 | Essinger et al. |
| 2010/0276493 A1 | 11/2010 | Havens et al. |
| 2011/0169999 A1 | 7/2011 | Grunow et al. |
| 2011/0202554 A1 | 8/2011 | Powilleit et al. |
| 2012/0111946 A1 | 5/2012 | Golant |
| 2012/0168512 A1 | 7/2012 | Kotlarsky et al. |
| 2012/0193423 A1 | 8/2012 | Samek |
| 2012/0203647 A1 | 8/2012 | Smith |
| 2012/0223141 A1 | 9/2012 | Good et al. |
| 2012/0281081 A1* | 11/2012 | Atif .................. G02B 27/0075 348/79 |
| 2012/0312877 A1* | 12/2012 | Zolotov .............. G06K 7/10722 235/462.04 |
| 2013/0043312 A1 | 2/2013 | Van Horn |
| 2013/0057753 A1* | 3/2013 | Gillet .................. H04N 5/23212 348/349 |
| 2013/0075168 A1 | 3/2013 | Amundsen et al. |
| 2013/0175341 A1 | 7/2013 | Kearney et al. |
| 2013/0175343 A1 | 7/2013 | Good |
| 2013/0257744 A1 | 10/2013 | Daghigh et al. |
| 2013/0257759 A1 | 10/2013 | Daghigh |
| 2013/0270346 A1 | 10/2013 | Xian et al. |
| 2013/0287258 A1 | 10/2013 | Kearney |
| 2013/0292475 A1 | 11/2013 | Kotlarsky et al. |
| 2013/0292477 A1 | 11/2013 | Hennick et al. |
| 2013/0293539 A1 | 11/2013 | Hunt et al. |
| 2013/0293540 A1 | 11/2013 | Laffargue et al. |
| 2013/0306728 A1 | 11/2013 | Thuries et al. |
| 2013/0306731 A1 | 11/2013 | Pedraro |
| 2013/0307964 A1 | 11/2013 | Bremer et al. |
| 2013/0308625 A1 | 11/2013 | Park et al. |
| 2013/0313324 A1 | 11/2013 | Koziol et al. |
| 2013/0313325 A1 | 11/2013 | Wilz et al. |
| 2013/0342717 A1 | 12/2013 | Havens et al. |
| 2014/0001267 A1 | 1/2014 | Giordano et al. |
| 2014/0002828 A1 | 1/2014 | Laffargue et al. |
| 2014/0008439 A1 | 1/2014 | Wang |
| 2014/0025584 A1 | 1/2014 | Liu et al. |
| 2014/0034734 A1 | 2/2014 | Sauerwein |
| 2014/0036848 A1 | 2/2014 | Pease et al. |
| 2014/0039693 A1 | 2/2014 | Havens et al. |
| 2014/0042814 A1 | 2/2014 | Kather et al. |
| 2014/0049120 A1 | 2/2014 | Kohtz et al. |
| 2014/0049635 A1 | 2/2014 | Laffargue et al. |
| 2014/0061306 A1 | 3/2014 | Wu et al. |
| 2014/0063289 A1 | 3/2014 | Hussey et al. |
| 2014/0066136 A1 | 3/2014 | Sauerwein et al. |
| 2014/0067692 A1 | 3/2014 | Ye et al. |
| 2014/0070005 A1 | 3/2014 | Nahill et al. |
| 2014/0071840 A1 | 3/2014 | Venancio |
| 2014/0074746 A1 | 3/2014 | Wang |
| 2014/0076974 A1 | 3/2014 | Havens et al. |
| 2014/0078341 A1 | 3/2014 | Havens et al. |
| 2014/0078342 A1 | 3/2014 | Li et al. |
| 2014/0078345 A1 | 3/2014 | Showering |
| 2014/0098792 A1 | 4/2014 | Wang et al. |
| 2014/0100774 A1 | 4/2014 | Showering |
| 2014/0100813 A1 | 4/2014 | Showering |
| 2014/0103115 A1 | 4/2014 | Meier et al. |
| 2014/0104413 A1 | 4/2014 | McCloskey et al. |
| 2014/0104414 A1 | 4/2014 | McCloskey et al. |
| 2014/0104416 A1 | 4/2014 | Giordano et al. |
| 2014/0104451 A1 | 4/2014 | Todeschini et al. |
| 2014/0106594 A1 | 4/2014 | Skvoretz |
| 2014/0106725 A1 | 4/2014 | Sauerwein |
| 2014/0108010 A1 | 4/2014 | Maltseff et al. |
| 2014/0108402 A1 | 4/2014 | Gomez et al. |
| 2014/0108682 A1 | 4/2014 | Caballero |

(56) References Cited

U.S. PATENT DOCUMENTS

| | | |
|---|---|---|
| 2014/0110485 A1 | 4/2014 | Toa et al. |
| 2014/0114530 A1 | 4/2014 | Fitch et al. |
| 2014/0124577 A1 | 5/2014 | Wang et al. |
| 2014/0124579 A1 | 5/2014 | Ding |
| 2014/0125842 A1 | 5/2014 | Winegar |
| 2014/0125853 A1 | 5/2014 | Wang |
| 2014/0125999 A1 | 5/2014 | Longacre et al. |
| 2014/0129378 A1 | 5/2014 | Richardson |
| 2014/0131438 A1 | 5/2014 | Kearney |
| 2014/0131441 A1 | 5/2014 | Nahill et al. |
| 2014/0131443 A1 | 5/2014 | Smith |
| 2014/0131444 A1 | 5/2014 | Wang |
| 2014/0131445 A1 | 5/2014 | Ding et al. |
| 2014/0131448 A1 | 5/2014 | Xian et al. |
| 2014/0133379 A1 | 5/2014 | Wang et al. |
| 2014/0136208 A1 | 5/2014 | Maltseff et al. |
| 2014/0140585 A1 | 5/2014 | Wang |
| 2014/0151453 A1 | 6/2014 | Meier et al. |
| 2014/0152882 A1 | 6/2014 | Samek et al. |
| 2014/0158770 A1 | 6/2014 | Sevier et al. |
| 2014/0159869 A1 | 6/2014 | Zumsteg et al. |
| 2014/0166755 A1 | 6/2014 | Liu et al. |
| 2014/0166757 A1 | 6/2014 | Smith |
| 2014/0166759 A1 | 6/2014 | Liu et al. |
| 2014/0168787 A1 | 6/2014 | Wang et al. |
| 2014/0175165 A1 | 6/2014 | Havens et al. |
| 2014/0175172 A1 | 6/2014 | Jovanovski et al. |
| 2014/0191644 A1 | 7/2014 | Chaney |
| 2014/0191913 A1 | 7/2014 | Ge et al. |
| 2014/0197238 A1 | 7/2014 | Liu et al. |
| 2014/0197239 A1 | 7/2014 | Havens et al. |
| 2014/0197304 A1 | 7/2014 | Feng et al. |
| 2014/0203087 A1 | 7/2014 | Smith et al. |
| 2014/0204268 A1 | 7/2014 | Grunow et al. |
| 2014/0214631 A1 | 7/2014 | Hansen |
| 2014/0217166 A1 | 8/2014 | Berthiaume et al. |
| 2014/0217180 A1 | 8/2014 | Liu |
| 2014/0231500 A1 | 8/2014 | Ehrhart et al. |
| 2014/0232930 A1 | 8/2014 | Anderson |
| 2014/0247315 A1 | 9/2014 | Marty et al. |
| 2014/0263493 A1 | 9/2014 | Amurgis et al. |
| 2014/0263645 A1 | 9/2014 | Smith et al. |
| 2014/0270196 A1 | 9/2014 | Braho et al. |
| 2014/0270229 A1 | 9/2014 | Braho |
| 2014/0278387 A1 | 9/2014 | DiGregorio |
| 2014/0282210 A1 | 9/2014 | Bianconi |
| 2014/0284384 A1 | 9/2014 | Lu et al. |
| 2014/0288933 A1 | 9/2014 | Braho et al. |
| 2014/0297058 A1 | 10/2014 | Barker et al. |
| 2014/0299665 A1 | 10/2014 | Barber et al. |
| 2014/0312121 A1 | 10/2014 | Lu et al. |
| 2014/0319220 A1 | 10/2014 | Coyle |
| 2014/0319221 A1 | 10/2014 | Oberpriller et al. |
| 2014/0326787 A1 | 11/2014 | Barten |
| 2014/0332590 A1 | 11/2014 | Wang et al. |
| 2014/0344943 A1 | 11/2014 | Todeschini et al. |
| 2014/0346233 A1 | 11/2014 | Liu et al. |
| 2014/0351317 A1 | 11/2014 | Smith et al. |
| 2014/0353373 A1 | 12/2014 | Van Horn et al. |
| 2014/0361073 A1 | 12/2014 | Qu et al. |
| 2014/0361082 A1 | 12/2014 | Xian et al. |
| 2014/0362184 A1 | 12/2014 | Jovanovski et al. |
| 2014/0363015 A1 | 12/2014 | Braho |
| 2014/0369511 A1 | 12/2014 | Sheerin et al. |
| 2014/0374483 A1 | 12/2014 | Lu |
| 2014/0374485 A1 | 12/2014 | Xian et al. |
| 2015/0001301 A1 | 1/2015 | Ouyang |
| 2015/0001304 A1 | 1/2015 | Todeschini |
| 2015/0003673 A1 | 1/2015 | Fletcher |
| 2015/0009338 A1 | 1/2015 | Laffargue et al. |
| 2015/0009610 A1 | 1/2015 | London et al. |
| 2015/0014416 A1 | 1/2015 | Kotlarsky et al. |
| 2015/0021397 A1 | 1/2015 | Rueblinger et al. |
| 2015/0028102 A1 | 1/2015 | Ren et al. |
| 2015/0028103 A1 | 1/2015 | Jiang |
| 2015/0028104 A1 | 1/2015 | Ma et al. |
| 2015/0029002 A1 | 1/2015 | Yeakley et al. |
| 2015/0032709 A1 | 1/2015 | Maloy et al. |
| 2015/0039309 A1 | 2/2015 | Braho et al. |
| 2015/0040378 A1 | 2/2015 | Saber et al. |
| 2015/0048168 A1 | 2/2015 | Fritz et al. |
| 2015/0049347 A1 | 2/2015 | Laffargue et al. |
| 2015/0051992 A1 | 2/2015 | Smith |
| 2015/0053766 A1 | 2/2015 | Havens et al. |
| 2015/0053768 A1 | 2/2015 | Wang et al. |
| 2015/0053769 A1 | 2/2015 | Thuries et al. |
| 2015/0062366 A1 | 3/2015 | Liu et al. |
| 2015/0063215 A1 | 3/2015 | Wang |
| 2015/0063676 A1 | 3/2015 | Lloyd et al. |
| 2015/0069130 A1 | 3/2015 | Gannon |
| 2015/0071819 A1 | 3/2015 | Todeschini |
| 2015/0083800 A1 | 3/2015 | Li et al. |
| 2015/0086114 A1 | 3/2015 | Todeschini |
| 2015/0088522 A1 | 3/2015 | Hendrickson et al. |
| 2015/0096872 A1 | 4/2015 | Woodburn |
| 2015/0099557 A1 | 4/2015 | Pettinelli et al. |
| 2015/0100196 A1 | 4/2015 | Hollifield |
| 2015/0102109 A1 | 4/2015 | Huck |
| 2015/0115035 A1 | 4/2015 | Meier et al. |
| 2015/0127791 A1 | 5/2015 | Kosecki et al. |
| 2015/0128116 A1 | 5/2015 | Chen et al. |
| 2015/0129659 A1 | 5/2015 | Feng et al. |
| 2015/0133047 A1 | 5/2015 | Smith et al. |
| 2015/0134470 A1 | 5/2015 | Hejl et al. |
| 2015/0136851 A1 | 5/2015 | Harding et al. |
| 2015/0136854 A1 | 5/2015 | Lu et al. |
| 2015/0142492 A1 | 5/2015 | Kumar |
| 2015/0144692 A1 | 5/2015 | Hejl |
| 2015/0144698 A1 | 5/2015 | Teng et al. |
| 2015/0144701 A1 | 5/2015 | Xian et al. |
| 2015/0149946 A1 | 5/2015 | Benos et al. |
| 2015/0161429 A1 | 6/2015 | Xian |
| 2015/0169925 A1 | 6/2015 | Chen et al. |
| 2015/0169929 A1 | 6/2015 | Williams et al. |
| 2015/0186703 A1 | 7/2015 | Chen et al. |
| 2015/0193644 A1 | 7/2015 | Kearney et al. |
| 2015/0193645 A1 | 7/2015 | Colavito et al. |
| 2015/0199957 A1 | 7/2015 | Funyak et al. |
| 2015/0204671 A1 | 7/2015 | Showering |
| 2015/0210199 A1 | 7/2015 | Payne |
| 2015/0220753 A1 | 8/2015 | Zhu et al. |
| 2015/0237270 A1* | 8/2015 | Atif .................. H04N 5/332 348/164 |
| 2015/0254485 A1 | 9/2015 | Feng et al. |
| 2015/0327012 A1 | 11/2015 | Bian et al. |
| 2016/0003675 A1 | 1/2016 | Abolbashari et al. |
| 2016/0014251 A1 | 1/2016 | Hejl |
| 2016/0040982 A1 | 2/2016 | Li et al. |
| 2016/0042241 A1 | 2/2016 | Todeschini |
| 2016/0057230 A1 | 2/2016 | Todeschini et al. |
| 2016/0109219 A1 | 4/2016 | Ackley et al. |
| 2016/0109220 A1 | 4/2016 | Laffargue |
| 2016/0109224 A1 | 4/2016 | Thuries et al. |
| 2016/0112631 A1 | 4/2016 | Ackley et al. |
| 2016/0112643 A1 | 4/2016 | Laffargue et al. |
| 2016/0124516 A1 | 5/2016 | Schoon et al. |
| 2016/0125217 A1 | 5/2016 | Todeschini |
| 2016/0125342 A1 | 5/2016 | Miller et al. |
| 2016/0125873 A1 | 5/2016 | Braho et al. |
| 2016/0133253 A1 | 5/2016 | Braho et al. |
| 2016/0171720 A1 | 6/2016 | Todeschini |
| 2016/0178479 A1 | 6/2016 | Goldsmith |
| 2016/0180678 A1 | 6/2016 | Ackley et al. |
| 2016/0189087 A1 | 6/2016 | Morton et al. |
| 2016/0227912 A1 | 8/2016 | Oberpriller et al. |
| 2016/0232891 A1 | 8/2016 | Pecorari |
| 2016/0291479 A1* | 10/2016 | Feijen ................ G01B 11/0616 |
| 2016/0292477 A1 | 10/2016 | Bidwell |
| 2016/0294779 A1 | 10/2016 | Yeakley et al. |
| 2016/0306769 A1 | 10/2016 | Kohtz et al. |
| 2016/0314276 A1 | 10/2016 | Wilz, Sr. et al. |

(56) References Cited

U.S. PATENT DOCUMENTS

2016/0314294 A1    10/2016    Kubler et al.
2017/0193727 A1    7/2017    Van Horn et al.

FOREIGN PATENT DOCUMENTS

| WO | 94/15184 A1 | 7/1994 |
|---|---|---|
| WO | 2011/138606 A1 | 11/2011 |
| WO | 2013163789 A1 | 11/2013 |
| WO | 2013173985 A1 | 11/2013 |
| WO | 2014019130 A1 | 2/2014 |
| WO | 2014110495 A1 | 7/2014 |

OTHER PUBLICATIONS

U.S. Appl. No. 29/525,068 for Tablet Computer With Removable Scanning Device filed Apr. 27, 2015 (Schulte et al.); 19 pages.
U.S. Appl. No. 29/468,118 for an Electronic Device Case, filed Sep. 26, 2013 (Oberpriller et al.); 44 pages.
U.S. Appl. No. 29/530,600 for Cyclone filed Jun. 18, 2015 (Vargo et al); 16 pages.
U.S. Appl. No. 14/707,123 for Application Independent DEX/UCS Interface filed May 8, 2015 (Pape); 47 pages.
U.S. Appl. No. 14/283,282 for Terminal Having Illumination and Focus Control filed May 21, 2014 (Liu et al.); 31 pages; now abandoned.
U.S. Appl. No. 14/705,407 for Method and System to Protect Software-Based Network-Connected Devices From Advanced Persistent Threat filed May 6, 2015 (Hussey et al.); 42 pages.
U.S. Appl. No. 14/704,050 for Intermediate Linear Positioning filed May 5, 2015 (Charpentier et al.); 60 pages.
U.S. Appl. No. 14/705,012 for Hands-Free Human Machine Interface Responsive to a Driver of a Vehicle filed May 6, 2015 (Fitch et al.); 44 pages.
U.S. Appl. No. 14/715,672 for Augumented Reality Enabled Hazard Display filed May 19, 2015 (Venkatesha et al.); 35 pages.
U.S. Appl. No. 14/735,717 for Indicia-Reading Systems Having an Interface With a User's Nervous System filed Jun. 10, 2015 (Todeschini); 39 pages.
U.S. Appl. No. 14/702,110 for System and Method for Regulating Barcode Data Injection Into a Running Application on a Smart Device filed May 1, 2015 (Todeschini et al.); 38 pages.
U.S. Appl. No. 14/747,197 for Optical Pattern Projector filed Jun. 23, 2015 (Thuries et al.); 33 pages.
U.S. Appl. No. 14/702,979 for Tracking Battery Conditions filed May 4, 2015 (Young et al.); 70 pages.
U.S. Appl. No. 29/529,441 for Indicia Reading Device filed Jun. 8, 2015 (Zhou et al.); 14 pages.
U.S. Appl. No. 14/747,490 for Dual-Projector Three-Dimensional Scanner filed Jun. 23, 2015 (Jovanovski et al.); 40 pages.
U.S. Appl. No. 14/740,320 for Tactile Switch for a Mobile Electronic Device filed Jun. 16, 2015 (Bamdringa); 38 pages.
U.S. Appl. No. 14/740,373 for Calibrating a Volume Dimensioner filed Jun. 16, 2015 (Ackley et al.); 63 pages.
U.S. Appl. No. 13/367,978, filed Feb. 7, 2012, (Feng et al.); now abandoned.
U.S. Appl. No. 14/277,337 for Multipurpose Optical Reader, filed May 14, 2014 (Jovanovski et al.); 59 pages; now abandoned.
U.S. Appl. No. 14/446,391 for Multifunction Point of Sale Apparatus With Optical Signature Capture filed Jul. 30, 2014 (Good et al.); 37 pages; now abandoned.
U.S. Appl. No. 29/516,892 for Table Computer filed Feb. 6, 2015 (Bidwell et al.); 13 pages.
U.S. Appl. No. 29/523,098 for Handle for a Tablet Computer filed Apr. 7, 2015 (Bidwell et al.); 17 pages.
U.S. Appl. No. 29/528,890 for Mobile Computer Housing filed Jun. 2, 2015 (Fitch et al.); 61 pages.
U.S. Appl. No. 29/526,918 for Charging Base filed May 14, 2015 (Fitch et al.); 10 pages.
Extended Search Report in related European Application No. 17150323.8 dated Jun. 14, 2017, pp. 1-7.

* cited by examiner

MULTI-SPECTRAL IMAGING USING LONGITUDINAL CHROMATIC ABERRATIONS

FIELD OF THE INVENTION

The present invention relates to systems and methods for imaging a target object and more particularly relates to multi-spectral imaging using longitudinal chromatic aberrations.

BACKGROUND

Generally speaking, multi-spectral imaging involves analyzing images at various wavelengths of light, such as visible light, ultraviolet light, and infrared light. Multi-spectral imaging can be used in many applications, such as for detecting counterfeit currency, detecting the quality of food, and other applications. The equipment used in many implementations of actual multi-spectral imaging typically includes spectrometers and/or rotating prisms. These implementations are normally very large and expensive. Therefore, a need exists for a more compact multi-spectral imaging device, especially one that can be handheld for easy use.

SUMMARY

Accordingly, the present invention embraces systems and methods for imaging an object. In one exemplary embodiment, an imaging device includes an objective lens and a sensor. The objective lens, having symmetry around an optical axis, is configured to disperse images of a target object in longitudinal chromatic aberrations along the optical axis. The sensor is configured to obtain multiple images of the target object, wherein each image corresponds to a specific wavelength within a predetermined spectrum.

In another exemplary embodiment, a method for imaging a target object is provided. The method includes a first step of optically dispersing multiple wavelengths of light reflected from a target object so as to create longitudinal chromatic aberrations on an optical axis, wherein each wavelength of the light corresponds to a point on the optical axis. The method also includes the step of sensing multiple in-focus images of the target object at the multiple wavelengths.

The foregoing illustrative summary, as well as other exemplary objectives and/or advantages of the invention, and the manner in which the same are accomplished, are further explained within the following detailed description and its accompanying drawings.

DETAILED DESCRIPTION

In the field of optics, the concept of chromatic aberration can be thought of as the result of a lens that fails to focus all colors to the same focal point. The effect of chromatic aberration occurs because of the difference in the refractive indices of different wavelengths of light. Instead of focusing the light to one point, a lens may disperse the light.

Additionally, longitudinal chromatic aberration is a type of chromatic aberration in which light is dispersed along a longitudinal axis, and more specifically, along the optical axis of a lens. For example, a lens that produces longitudinal chromatic aberrations focuses rays of light having wavelengths at one end of the spectrum farthest from the rays of light having wavelengths at the other end of the spectrum. The present invention takes advantage of the phenomenon of longitudinal chromatic aberrations to obtain multiple images at different wavelengths corresponding to the focal point or focal field of the particular wavelength.

The present invention embraces systems and methods for obtaining images of a target object at various wavelengths and analyzing the images to determine certain characteristics of the target object. The present invention may include a lens, such as an objective lens, that is designed to disperse light without correcting for chromatic aberrations. Specifically, the objective lens of the present invention may provide longitudinal chromatic aberrations, such that light at different wavelengths is focused at different points along the optical axis of the lens. The present invention may also include a sensor configured to obtain multiple in-focus images of the object at the different wavelengths. In some embodiments, the sensor is moved along the optical axis to obtain the images.

From the multiple images, an image stack can be generated. The image stack can then be used to analyze various properties to detect characteristics of the object. In one example, specific portions of images at specific wavelengths can be analyzed to determine whether or not printed currency is counterfeit. Also, the quality or maturity of food can be analyzed by observing the absorption spectrum.

Figure 1:
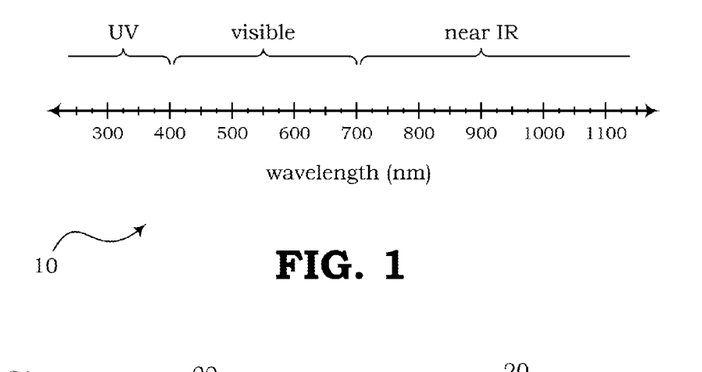
FIG. 1 schematically depicts a chart showing the relevant wavelengths of electromagnetic radiation being monitored according to at least one embodiment of the present invention.

FIG. 1 is a chart showing the wavelengths of electromagnetic radiation within a specific spectrum 10 according to exemplary embodiments. The spectrum 10 corresponds substantially to the relevant wavelengths utilized by the present invention. In particular, with the use of a CMOS sensor, the relevant wavelengths may range from about 300 nm to about 1100. Therefore, the spectrum 10 in this example encompasses the entire visible spectrum, which ranges from about 400 nm to about 700 nm and also includes part of the ultraviolet (UV) spectrum, which includes wavelengths below 400 nm, and part of the near infrared (near IR) spectrum, which includes wavelengths above 700 nm.

According to some embodiments, other types of sensors may be used to sense a wider range of wavelengths. For example, some sensors may be used to sense lower wavelengths in the UV spectrum, which includes wavelengths from about 100 nm to 400 nm, and higher wavelengths in the IR spectrum, which includes wavelengths from about 700 nm to about 1 mm.

The present invention may provide a source of light for illuminating a target object. In some embodiments, the light source may provide a range of electromagnetic radiation ranging from about 300 nm to about 1100 nm. Also, the optical systems of the present invention may be capable of sensing at least the same range as shown by the spectrum 10 in FIG. 1. In some embodiments, the optical systems may be configured to sense a greater range of electromagnetic radiation.

Figure 2:
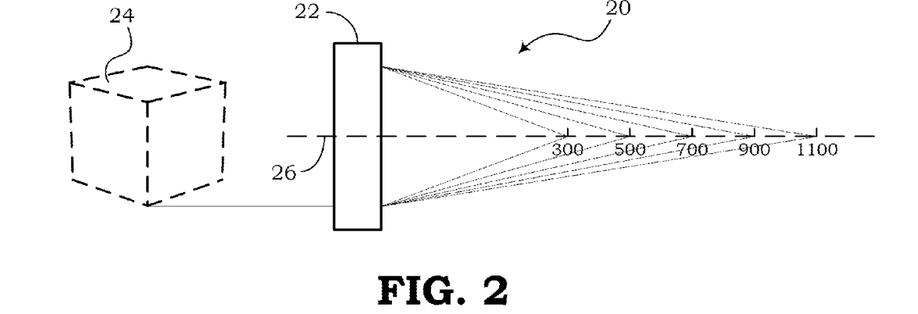
FIG. 2 schematically depicts a diagram of a multi-spectral imaging apparatus according to at least one embodiment of the present invention.

FIG. 2 is a diagram of an apparatus 20 illustrating an example of the general concepts of the present invention and more particularly the concepts of an objective lens that may be utilized in the various embodiments of the present invention. The apparatus 20 includes a chromatic aberration unit 22, which represents an optical system for imaging a target object 24. The chromatic aberration unit 22 includes an optical axis 26, which defines an imaginary line about which the optical elements of the chromatic aberration unit 22 are rotationally symmetrical.

As shown in FIG. 2, light rays reflected from the target object 24 are radiated to the chromatic aberration unit 22. The chromatic aberration unit 22 optically refracts the rays such that different wavelengths are focused at different points along the optical axis 26. According to some embodiments, such as those illustrated in FIGS. 5 and 6, the chromatic aberration unit 22 may further include optical components in additional to an objective lens for correcting for the longitudinal chromatic aberrations. By correcting for the longitudinal chromatic aberrations, images at all relevant wavelengths can be focused onto one point on the optical axis 26. It should be noted that the depth of focus at each wavelength enables a sensor to distinguish a sharp image from a blurred image.

The chromatic aberration unit 22 of FIG. 2 may include various combinations of lenses, filters, etc., depending on the various embodiments, as described in more detail below. Regardless of the particular implementation, the chromatic aberration unit 22 includes an objective lens that is configured to optically disperse an image of the target object 24. The dispersion of the image includes focusing specific wavelengths of the image onto specific points along the optical axis 26. For example, the chromatic aberration unit 22 is capable of focusing an ultraviolet image having a wavelength of 300 nm onto the optical axis at the point marked "300" in FIG. 2.

Although the numerals "300," "500," "700", etc. are shown in FIG. 2, it should be noted that they are not part of the apparatus 20 itself, but are shown mainly for the purpose of explanation. Also, the optical axis 26 is an imaginary line and is also shown for the purpose of explanation. It should be noted that the scale regarding the corresponding wavelengths at the points along the optical axis 26 may not necessarily be a linear scale, as shown, but may rather depend on the characteristics of the chromatic aberration unit 22.

Depending on the configuration of the chromatic aberration unit 22, images of the target object 24 may be dispersed at any wavelengths between about 300 nm and 1100 nm. Also, the chromatic aberration unit 22 may also be configured to disperse other wavelengths less than 300 nm and/or greater than 1100 nm along the optical axis 26.

Figure 3:
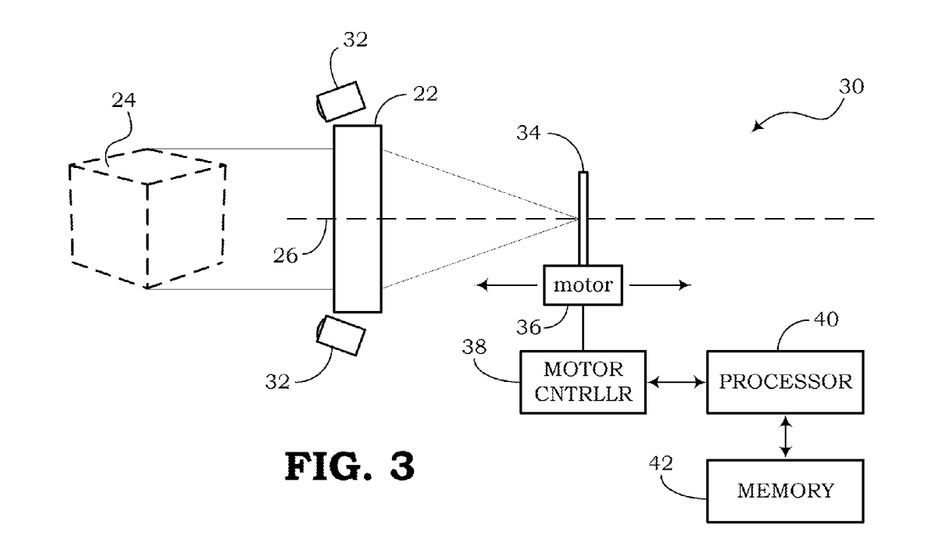
FIG. 3 schematically depicts a diagram of an optical imager according to at least a first embodiment of the present invention.

FIG. 3 is a diagram showing a first embodiment of an optical imager 30. The optical imager 30 includes the chromatic aberration unit 22 having optical axis 26, as described above with respect to FIG. 2. The optical imager 30 further includes one or more radiation sources 32, a sensor 34, a motor 36, a motor controller 38, a processor 40, and memory 42. The sensor 34, motor 36, and motor controller 38 may define an auto-focus mechanism. Other types of auto-focus mechanisms may be utilized in the present invention for moving the sensor 34 reciprocally along the optical axis 26. The purpose of the auto-focus mechanism is to enable the sensor 34 to acquire in-focus images at different wavelengths by moving the sensor 34 along the caustic of chromatic aberration created by the optical system.

The radiation sources 32 define a broadband spectrum source when considered in combination or separately. Therefore, the radiation sources 32 are configured to illuminate the target object 24 with light within the relevant spectrum utilized by the optical imager 30, which may include electromagnetic radiation ranging in wavelength from about 300 nm to about 1100 nm. As mentioned above, the chromatic aberration unit 22 disperses the light rays based on wavelength. Shorter wavelength (e.g., ultraviolet) refract at a greater angle than longer wavelengths (e.g., near IR) and are focused at different points on the optical axis 26.

In some embodiments, the sensor 34 may be a CMOS sensing component, which may be configured to sense electromagnetic radiation in a range from about 300 nm to about 1100 nm. According to other embodiments, the sensor 34 may include other types of sensing components for sensing wavelengths below 300 nm and/or for sensing wavelengths above 1100 nm.

The processor 40 instructs the motor controller 38 to cause the motor 36 to move the sensor 34 in a reciprocal motion along the optical axis 26. In some embodiments, the motor controller 38 may control the motor 36 to move in a stepwise manner. Accordingly, the motor 36 may be configured to move the sensor 34 to a first point where the light is sensed with respect to a first wavelength, then move the sensor 34 to a second point where the light is sensed with respect to a second wavelength, and so on. This can be repeated for multiple wavelengths within the relevant spectrum.

For example, the optical imager 30 may be configured to step the sensor 34 in such a way as to capture images of the target object 24 with respect to various wavelengths differing by about 25 nm. When sensed at 25 nm apart (i.e., at each tick mark in FIG. 1), the optical imager 30 may capture, for example, 41 images from 300 nm to 1100 nm. The processor 40 may further be configured to store the captured images in the memory device 42.

Figure 4A:
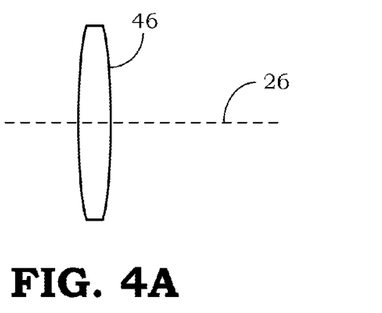
FIGS. 4A and 4B schematically depict diagrams of the chromatic aberration units shown in FIGS. 2 and 3 according to various embodiments of the present invention.

FIG. 4A illustrates a first embodiment of the chromatic aberration unit 22 shown in FIGS. 2 and 3. In this embodiment, the chromatic aberration unit 22 may be configured as a single objective lens 46 symmetrically arranged with the optical axis 26. The objective lens 46 may be designed to specifically refract light of various wavelengths at different refractive indices so as to disperse the different wavelengths of light. The objective lens 46 disperses the light without the conventional practice of attempting to correct for chromatic aberrations.

Figure 4B:
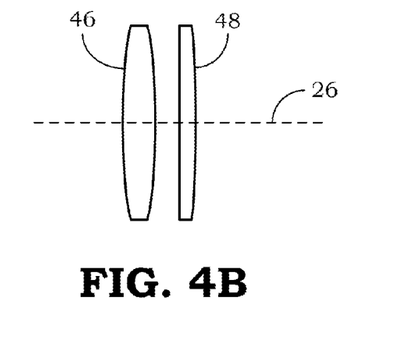

FIG. 4B illustrates a second embodiment of the chromatic aberration unit 22 shown in FIGS. 2 and 3. In this embodiment, the chromatic aberration unit 22 may be configured as a combination of lenses, such as a common objective lens 46 and a diffraction lens 48. In other embodiments, three or more lenses may be used. Also, the chromatic aberration unit 22 may include one or more filters for filtering out unwanted wavelengths of electromagnetic radiation.

Figure 5:
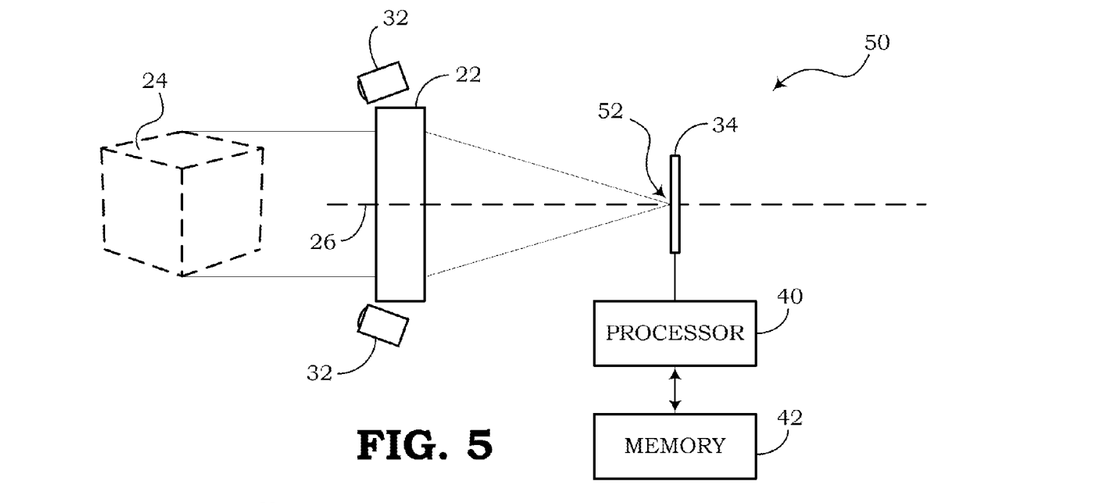
FIG. 5 schematically depicts a diagram of an optical imager according to at least a second embodiment of the present invention.

FIG. 5 illustrates a diagram of a second embodiment of an optical imager 50. In the embodiment of FIG. 5, the chromatic aberration unit 22 may include features in addition to the lenses and filters described with respect to FIGS. 4A and 4B. For example, the chromatic aberration unit 22 in FIG. 5 may further include an autofocusing component that focuses the dispersed light onto one point 52 on the optical axis 26. Therefore, the motor 36 and motor controller 38 shown in FIG. 3 is not needed in this embodiment and the sensor 34 remains stationary.

In this embodiment, the processor 40 may be configured to control the focusing components of the chromatic aberration unit 22 for a particular wavelength and store the image sensed by the sensor 34 at the particular wavelength into memory 42. This process can be repeated for multiple wavelengths such that the processor-controlled auto-focusing components of the chromatic aberration unit 22 changes for each wavelength being sensed.

Various technologies, as discussed below, can be used to provide auto-focusing without the use of mechanically manipulating the sensor 34. Therefore, the non-moving devices can replace the mechanical actuator described with respect to FIG. 3. Implementing an autofocus mechanism without any moving part may be more robust than the mechanical type.

Figure 6A:
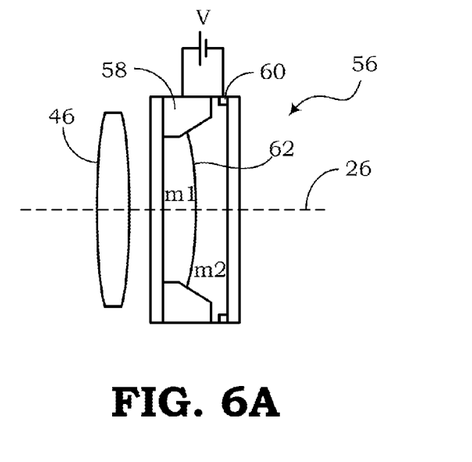
FIGS. 6A and 6B schematically depict diagrams of the chromatic aberration units shown in FIG. 5 according to various embodiments of the present invention.

FIG. 6A is a diagram showing an embodiment of a liquid lens 56 that may be used with the objective lens 46 for auto-focusing purposes. Based on input from the processor 40, the physical properties of the liquid lens 56 can be changed. The changes in physical properties thereby change the optical characteristics of the liquid lens 56 to enable focusing the light rays of different wavelengths on the single point 52.

The liquid lens 56 includes a fluid-tight structure that contains a first medium m1 and a second medium m2 separated from each other by a natural barrier 62. For example, the first medium m1 may be water and the second medium m2 may be oil. When the processor 40 applies a voltage V across metal terminals 58 and 60, the media m1, m2 react such that the curvature of the natural barrier 62 changes. For example, a low voltage will cause the first medium m1 to take on a concave shape whereas a high voltage will cause the first medium m1 to take on a convex shape. Light passing through the liquid lens 56 is refracted based on the controlled curvature of the barrier 62 between m1 and m2.

In operation, the objective lens 46 may disperse the light rays based on wavelength as mentioned above. Then, the liquid lens 56 can be adjusted to compensate for the chromatic aberrations. The liquid lens 56 can be controlled so as to focus the light of each respective wavelength onto the point (shown in FIG. 5) on the optical axis 26. Therefore, specific voltages can be applied across the terminals 58, 60 to achieve a desired curvature of the barrier 62 to focus the light of various wavelengths onto the point 52.

According to other embodiments, the liquid lens may be configured using the electro-wetting principle to achieve an auto-focusing device. Other types of auto-focusing devices can be implemented using other known principles.

Figure 6B:
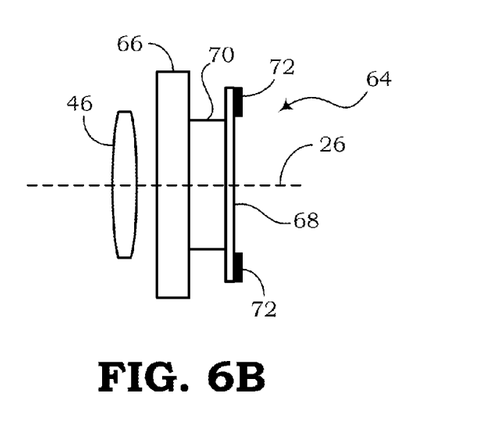

FIG. 6B is a diagram of an embodiment of a deformable lens 64. The objective lens 46 may also be used in this embodiment for dispersing the light, as mentioned above. The deformable lens 64 in this embodiment includes a glass base 66, a thin glass layer 68, and a soft polymer 70 between the glass base 66 and thin glass layer 68. The deformable lens 64 also includes one or more piezo-electric elements 72 formed around the edges of the thin glass layer 68.

The piezo-electric elements 72 applies forces on the thin glass layer 68 based on the voltage applied to the piezo-electric elements 72. At zero volts, the piezo-electric elements 72 do not apply any force. As the voltage is increased, the piezo-electric elements 72 deform or bend the thin glass layer 68 to various degrees depending on the voltage applied. The bending of the thin glass layer 68 changes the optical focus. Therefore, the processor 40 is configured to control the deformable lens 64 to adjust the focus as needed to maintain the focal point of the corresponding wavelength being measured to the point 52 where the sensor 34 is located.

In other embodiments, the deformable lens may include first and second liquid media m1, m2, separated by a natural barrier. In this embodiment, a piezo-electric element 66 can be stimulated to cause it to press against a depressible wall at various pressures. The depressible wall can be depressed to various degrees causing the pressure of one medium to bulge out toward the other, depending on the particular pressure within the chambers in which the media m1, m2 are contained, thereby changing the optical properties and enabling auto-focus.

Figure 7:
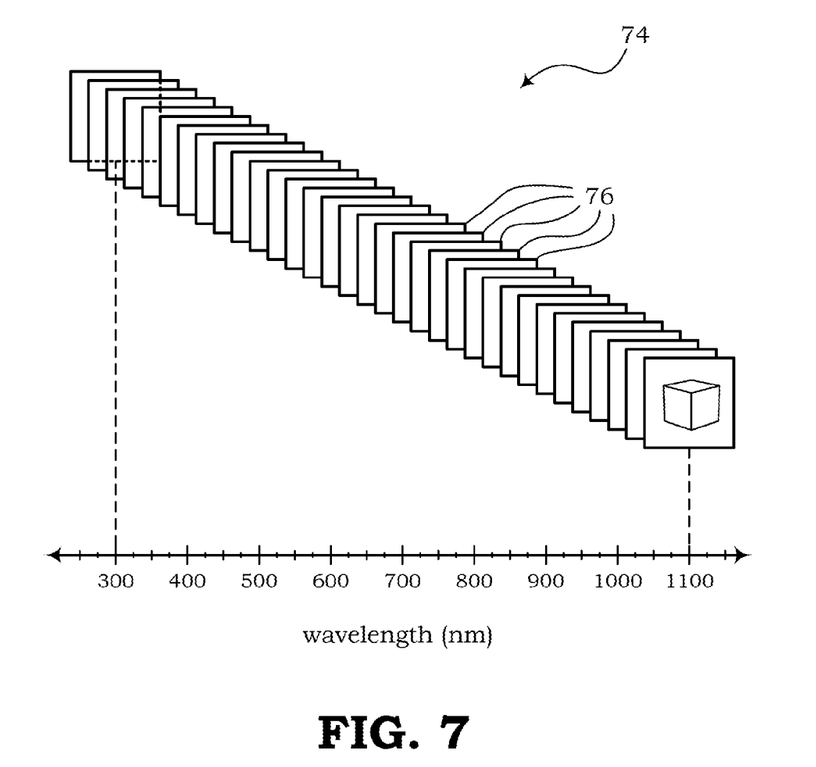
FIG. 7 schematically depicts a diagram of an image stack according to at least one embodiment of the present invention.

FIG. 7 is a diagram showing an example of an image stack 74 comprising multiple images 76 of the target object 24. Each image 76 represents an in-focus view of the target object 24 at a corresponding wavelength. According to the embodiments in connection with FIGS. 3 and 4, the multiple images 76 may be captured at various points along the optical axis 26. According to the embodiments in connection with FIGS. 5 and 6, the multiple images 76 may be captured at the same point on the optical axis 26, but may be automatically focused on the point based on the particular wavelength being sensed.

The image stack 74 is a three-dimensional multi-spectral image that stacks the images 76 acquired at various steps within the relevant spectrum. Images are acquired at the wavelengths within the relevant spectrum of about 300 nm to about 1100 nm, as described above. The images 76 do not necessarily include every wavelength, but include discrete measurements within the spectrum.

Once the three-dimensional image stack 74 is obtained at the multiple wavelengths, various properties of the target object 24 can be analyzed. For detecting counterfeit bills, different regions of the bill can be analyzed by the processor 40 at one or more wavelengths and compared with the corresponding regions of a real bill.

For food quality detection, absorption of various wavelengths can be analyzed. For example, as a fruit gets mature, its absorption of various light may vary. Therefore, the fruit can be analyzed for ripeness as well as being analyzed for past a ripe stage into turning rotten.

Other applications of multi-spectral imaging can be implemented. Particularly, the uses may be especially more convenient using a the multi-spectral imaging devices described in the present disclosure since the embodiments described herein may be embodied in a compact, handheld device, as described below.

Figure 8:
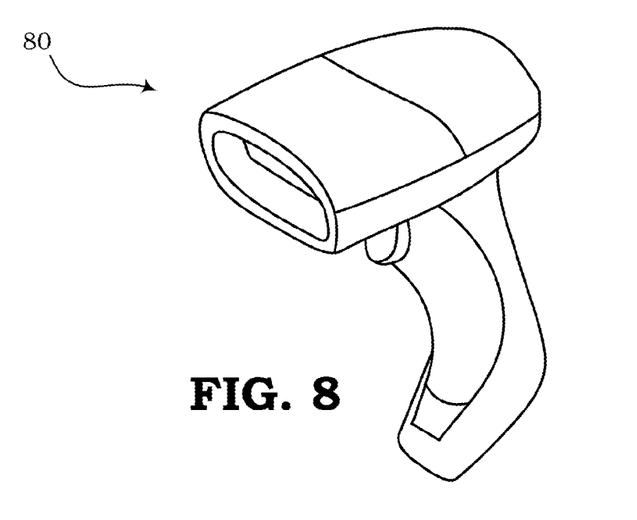
FIG. 8 schematically depicts a diagram of a handheld device for housing an optical imager, according to at least one embodiment of the present invention.

FIG. 8 is a diagram of an example of a handheld device 80 configured to house the optical imager 30, 50. The embodiments described in the present disclosure represent a great reduction in size with respect to conventional optical imagers. In this respect, a user can easily manipulate the handheld device 80 to capture the three-dimensional image stack 74 of the target object 24 at multiple wavelengths. The handheld device 80 is also configured to process the images to determine various properties of the target object 24.

In some embodiments, the handheld device 80 may also be configured to house barcode scanning circuitry in addition to the optical imager 30, 50. Therefore, a user may be able to scan a barcode and perform multi-spectral imaging using a single device.

To supplement the present disclosure, this application incorporates entirely by reference the following commonly assigned patents, patent application publications, and patent applications:

U.S. Pat. No. 6,832,725; U.S. Pat. No. 7,128,266;
U.S. Pat. No. 7,159,783; U.S. Pat. No. 7,413,127;
U.S. Pat. No. 7,726,575; U.S. Pat. No. 8,294,969;
U.S. Pat. No. 8,317,105; U.S. Pat. No. 8,322,622;
U.S. Pat. No. 8,366,005; U.S. Pat. No. 8,371,507;
U.S. Pat. No. 8,376,233; U.S. Pat. No. 8,381,979;
U.S. Pat. No. 8,390,909; U.S. Pat. No. 8,408,464;
U.S. Pat. No. 8,408,468; U.S. Pat. No. 8,408,469;
U.S. Pat. No. 8,424,768; U.S. Pat. No. 8,448,863;
U.S. Pat. No. 8,457,013; U.S. Pat. No. 8,459,557;
U.S. Pat. No. 8,469,272; U.S. Pat. No. 8,474,712;
U.S. Pat. No. 8,479,992; U.S. Pat. No. 8,490,877;
U.S. Pat. No. 8,517,271; U.S. Pat. No. 8,523,076;
U.S. Pat. No. 8,528,818; U.S. Pat. No. 8,544,737;
U.S. Pat. No. 8,548,242; U.S. Pat. No. 8,548,420;
U.S. Pat. No. 8,550,335; U.S. Pat. No. 8,550,354;
U.S. Pat. No. 8,550,357; U.S. Pat. No. 8,556,174;
U.S. Pat. No. 8,556,176; U.S. Pat. No. 8,556,177;
U.S. Pat. No. 8,559,767; U.S. Pat. No. 8,599,957;
U.S. Pat. No. 8,561,895; U.S. Pat. No. 8,561,903;
U.S. Pat. No. 8,561,905; U.S. Pat. No. 8,565,107;
U.S. Pat. No. 8,571,307; U.S. Pat. No. 8,579,200;
U.S. Pat. No. 8,583,924; U.S. Pat. No. 8,584,945;
U.S. Pat. No. 8,587,595; U.S. Pat. No. 8,587,697;
U.S. Pat. No. 8,588,869; U.S. Pat. No. 8,590,789;
U.S. Pat. No. 8,596,539; U.S. Pat. No. 8,596,542;
U.S. Pat. No. 8,596,543; U.S. Pat. No. 8,599,271;
U.S. Pat. No. 8,599,957; U.S. Pat. No. 8,600,158;
U.S. Pat. No. 8,600,167; U.S. Pat. No. 8,602,309;
U.S. Pat. No. 8,608,053; U.S. Pat. No. 8,608,071;
U.S. Pat. No. 8,611,309; U.S. Pat. No. 8,615,487;
U.S. Pat. No. 8,616,454; U.S. Pat. No. 8,621,123;
U.S. Pat. No. 8,622,303; U.S. Pat. No. 8,628,013;
U.S. Pat. No. 8,628,015; U.S. Pat. No. 8,628,016;
U.S. Pat. No. 8,629,926; U.S. Pat. No. 8,630,491;
U.S. Pat. No. 8,635,309; U.S. Pat. No. 8,636,200;
U.S. Pat. No. 8,636,212; U.S. Pat. No. 8,636,215;
U.S. Pat. No. 8,636,224; U.S. Pat. No. 8,638,806;
U.S. Pat. No. 8,640,958; U.S. Pat. No. 8,640,960;
U.S. Pat. No. 8,643,717; U.S. Pat. No. 8,646,692;
U.S. Pat. No. 8,646,694; U.S. Pat. No. 8,657,200;
U.S. Pat. No. 8,659,397; U.S. Pat. No. 8,668,149;
U.S. Pat. No. 8,678,285; U.S. Pat. No. 8,678,286;
U.S. Pat. No. 8,682,077; U.S. Pat. No. 8,687,282;
U.S. Pat. No. 8,692,927; U.S. Pat. No. 8,695,880;
U.S. Pat. No. 8,698,949; U.S. Pat. No. 8,717,494;
U.S. Pat. No. 8,717,494; U.S. Pat. No. 8,720,783;
U.S. Pat. No. 8,723,804; U.S. Pat. No. 8,723,904;
U.S. Pat. No. 8,727,223; U.S. Pat. No. D702,237;
U.S. Pat. No. 8,740,082; U.S. Pat. No. 8,740,085;
U.S. Pat. No. 8,746,563; U.S. Pat. No. 8,750,445;
U.S. Pat. No. 8,752,766; U.S. Pat. No. 8,756,059;
U.S. Pat. No. 8,757,495; U.S. Pat. No. 8,760,563;
U.S. Pat. No. 8,763,909; U.S. Pat. No. 8,777,108;
U.S. Pat. No. 8,777,109; U.S. Pat. No. 8,779,898;
U.S. Pat. No. 8,781,520; U.S. Pat. No. 8,783,573;
U.S. Pat. No. 8,789,757; U.S. Pat. No. 8,789,758;
U.S. Pat. No. 8,789,759; U.S. Pat. No. 8,794,520;
U.S. Pat. No. 8,794,522; U.S. Pat. No. 8,794,525;
U.S. Pat. No. 8,794,526; U.S. Pat. No. 8,798,367;
U.S. Pat. No. 8,807,431; U.S. Pat. No. 8,807,432;
U.S. Pat. No. 8,820,630; U.S. Pat. No. 8,822,848;
U.S. Pat. No. 8,824,692; U.S. Pat. No. 8,824,696;
U.S. Pat. No. 8,842,849; U.S. Pat. No. 8,844,822;
U.S. Pat. No. 8,844,823; U.S. Pat. No. 8,849,019;
U.S. Pat. No. 8,851,383; U.S. Pat. No. 8,854,633;
U.S. Pat. No. 8,866,963; U.S. Pat. No. 8,868,421;
U.S. Pat. No. 8,868,519; U.S. Pat. No. 8,868,802;
U.S. Pat. No. 8,868,803; U.S. Pat. No. 8,870,074;
U.S. Pat. No. 8,879,639; U.S. Pat. No. 8,880,426;
U.S. Pat. No. 8,881,983; U.S. Pat. No. 8,881,987;
U.S. Pat. No. 8,903,172; U.S. Pat. No. 8,908,995;
U.S. Pat. No. 8,910,870; U.S. Pat. No. 8,910,875;
U.S. Pat. No. 8,914,290; U.S. Pat. No. 8,914,788;
U.S. Pat. No. 8,915,439; U.S. Pat. No. 8,915,444;
U.S. Pat. No. 8,916,789; U.S. Pat. No. 8,918,250;
U.S. Pat. No. 8,918,564; U.S. Pat. No. 8,925,818;
U.S. Pat. No. 8,939,374; U.S. Pat. No. 8,942,480;
U.S. Pat. No. 8,944,313; U.S. Pat. No. 8,944,327;
U.S. Pat. No. 8,944,332; U.S. Pat. No. 8,950,678;
U.S. Pat. No. 8,967,468; U.S. Pat. No. 8,971,346;
U.S. Pat. No. 8,976,030; U.S. Pat. No. 8,976,368;
U.S. Pat. No. 8,978,981; U.S. Pat. No. 8,978,983;
U.S. Pat. No. 8,978,984; U.S. Pat. No. 8,985,456;
U.S. Pat. No. 8,985,457; U.S. Pat. No. 8,985,459;
U.S. Pat. No. 8,985,461; U.S. Pat. No. 8,988,578;
U.S. Pat. No. 8,988,590; U.S. Pat. No. 8,991,704;
U.S. Pat. No. 8,996,194; U.S. Pat. No. 8,996,384;
U.S. Pat. No. 9,002,641; U.S. Pat. No. 9,007,368;
U.S. Pat. No. 9,010,641; U.S. Pat. No. 9,015,513;
U.S. Pat. No. 9,016,576; U.S. Pat. No. 9,022,288;
U.S. Pat. No. 9,030,964; U.S. Pat. No. 9,033,240;
U.S. Pat. No. 9,033,242; U.S. Pat. No. 9,036,054;
U.S. Pat. No. 9,037,344; U.S. Pat. No. 9,038,911;
U.S. Pat. No. 9,038,915; U.S. Pat. No. 9,047,098;
U.S. Pat. No. 9,047,359; U.S. Pat. No. 9,047,420;
U.S. Pat. No. 9,047,525; U.S. Pat. No. 9,047,531;
U.S. Pat. No. 9,053,055; U.S. Pat. No. 9,053,378;
U.S. Pat. No. 9,053,380; U.S. Pat. No. 9,058,526;
U.S. Pat. No. 9,064,165; U.S. Pat. No. 9,064,167;
U.S. Pat. No. 9,064,168; U.S. Pat. No. 9,064,254;
U.S. Pat. No. 9,066,032; U.S. Pat. No. 9,070,032;
U.S. Design Pat. No. D716,285;
U.S. Design Pat. No. D723,560;
U.S. Design Pat. No. D730,357;
U.S. Design Pat. No. D730,901;
U.S. Design Pat. No. D730,902;
U.S. Design Pat. No. D733,112;
U.S. Design Pat. No. D734,339;
International Publication No. 2013/163789;
International Publication No. 2013/173985;
International Publication No. 2014/019130;
International Publication No. 2014/110495;
U.S. Patent Application Publication No. 2008/0185432;
U.S. Patent Application Publication No. 2009/0134221;
U.S. Patent Application Publication No. 2010/0177080;
U.S. Patent Application Publication No. 2010/0177076;
U.S. Patent Application Publication No. 2010/0177707;
U.S. Patent Application Publication No. 2010/0177749;
U.S. Patent Application Publication No. 2010/0265880;
U.S. Patent Application Publication No. 2011/0202554;
U.S. Patent Application Publication No. 2012/0111946;
U.S. Patent Application Publication No. 2012/0168511;

U.S. Patent Application Publication No. 2012/0168512;
U.S. Patent Application Publication No. 2012/0193423;
U.S. Patent Application Publication No. 2012/0203647;
U.S. Patent Application Publication No. 2012/0223141;
U.S. Patent Application Publication No. 2012/0228382;
U.S. Patent Application Publication No. 2012/0248188;
U.S. Patent Application Publication No. 2013/0043312;
U.S. Patent Application Publication No. 2013/0082104;
U.S. Patent Application Publication No. 2013/0175341;
U.S. Patent Application Publication No. 2013/0175343;
U.S. Patent Application Publication No. 2013/0257744;
U.S. Patent Application Publication No. 2013/0257759;
U.S. Patent Application Publication No. 2013/0270346;
U.S. Patent Application Publication No. 2013/0287258;
U.S. Patent Application Publication No. 2013/0292475;
U.S. Patent Application Publication No. 2013/0292477;
U.S. Patent Application Publication No. 2013/0293539;
U.S. Patent Application Publication No. 2013/0293540;
U.S. Patent Application Publication No. 2013/0306728;
U.S. Patent Application Publication No. 2013/0306731;
U.S. Patent Application Publication No. 2013/0307964;
U.S. Patent Application Publication No. 2013/0308625;
U.S. Patent Application Publication No. 2013/0313324;
U.S. Patent Application Publication No. 2013/0313325;
U.S. Patent Application Publication No. 2013/0342717;
U.S. Patent Application Publication No. 2014/0001267;
U.S. Patent Application Publication No. 2014/0008439;
U.S. Patent Application Publication No. 2014/0025584;
U.S. Patent Application Publication No. 2014/0034734;
U.S. Patent Application Publication No. 2014/0036848;
U.S. Patent Application Publication No. 2014/0039693;
U.S. Patent Application Publication No. 2014/0042814;
U.S. Patent Application Publication No. 2014/0049120;
U.S. Patent Application Publication No. 2014/0049635;
U.S. Patent Application Publication No. 2014/0061306;
U.S. Patent Application Publication No. 2014/0063289;
U.S. Patent Application Publication No. 2014/0066136;
U.S. Patent Application Publication No. 2014/0067692;
U.S. Patent Application Publication No. 2014/0070005;
U.S. Patent Application Publication No. 2014/0071840;
U.S. Patent Application Publication No. 2014/0074746;
U.S. Patent Application Publication No. 2014/0076974;
U.S. Patent Application Publication No. 2014/0078341;
U.S. Patent Application Publication No. 2014/0078345;
U.S. Patent Application Publication No. 2014/0097249;
U.S. Patent Application Publication No. 2014/0098792;
U.S. Patent Application Publication No. 2014/0100813;
U.S. Patent Application Publication No. 2014/0103115;
U.S. Patent Application Publication No. 2014/0104413;
U.S. Patent Application Publication No. 2014/0104414;
U.S. Patent Application Publication No. 2014/0104416;
U.S. Patent Application Publication No. 2014/0104451;
U.S. Patent Application Publication No. 2014/0106594;
U.S. Patent Application Publication No. 2014/0106725;
U.S. Patent Application Publication No. 2014/0108010;
U.S. Patent Application Publication No. 2014/0108402;
U.S. Patent Application Publication No. 2014/0110485;
U.S. Patent Application Publication No. 2014/0114530;
U.S. Patent Application Publication No. 2014/0124577;
U.S. Patent Application Publication No. 2014/0124579;
U.S. Patent Application Publication No. 2014/0125842;
U.S. Patent Application Publication No. 2014/0125853;
U.S. Patent Application Publication No. 2014/0125999;
U.S. Patent Application Publication No. 2014/0129378;
U.S. Patent Application Publication No. 2014/0131438;
U.S. Patent Application Publication No. 2014/0131441;
U.S. Patent Application Publication No. 2014/0131443;
U.S. Patent Application Publication No. 2014/0131444;
U.S. Patent Application Publication No. 2014/0131445;
U.S. Patent Application Publication No. 2014/0131448;
U.S. Patent Application Publication No. 2014/0133379;
U.S. Patent Application Publication No. 2014/0136208;
U.S. Patent Application Publication No. 2014/0140585;
U.S. Patent Application Publication No. 2014/0151453;
U.S. Patent Application Publication No. 2014/0152882;
U.S. Patent Application Publication No. 2014/0158770;
U.S. Patent Application Publication No. 2014/0159869;
U.S. Patent Application Publication No. 2014/0166755;
U.S. Patent Application Publication No. 2014/0166759;
U.S. Patent Application Publication No. 2014/0168787;
U.S. Patent Application Publication No. 2014/0175165;
U.S. Patent Application Publication No. 2014/0175172;
U.S. Patent Application Publication No. 2014/0191644;
U.S. Patent Application Publication No. 2014/0191913;
U.S. Patent Application Publication No. 2014/0197238;
U.S. Patent Application Publication No. 2014/0197239;
U.S. Patent Application Publication No. 2014/0197304;
U.S. Patent Application Publication No. 2014/0214631;
U.S. Patent Application Publication No. 2014/0217166;
U.S. Patent Application Publication No. 2014/0217180;
U.S. Patent Application Publication No. 2014/0231500;
U.S. Patent Application Publication No. 2014/0232930;
U.S. Patent Application Publication No. 2014/0247315;
U.S. Patent Application Publication No. 2014/0263493;
U.S. Patent Application Publication No. 2014/0263645;
U.S. Patent Application Publication No. 2014/0267609;
U.S. Patent Application Publication No. 2014/0270196;
U.S. Patent Application Publication No. 2014/0270229;
U.S. Patent Application Publication No. 2014/0278387;
U.S. Patent Application Publication No. 2014/0278391;
U.S. Patent Application Publication No. 2014/0282210;
U.S. Patent Application Publication No. 2014/0284384;
U.S. Patent Application Publication No. 2014/0288933;
U.S. Patent Application Publication No. 2014/0297058;
U.S. Patent Application Publication No. 2014/0299665;
U.S. Patent Application Publication No. 2014/0312121;
U.S. Patent Application Publication No. 2014/0319220;
U.S. Patent Application Publication No. 2014/0319221;
U.S. Patent Application Publication No. 2014/0326787;
U.S. Patent Application Publication No. 2014/0332590;
U.S. Patent Application Publication No. 2014/0344943;
U.S. Patent Application Publication No. 2014/0346233;
U.S. Patent Application Publication No. 2014/0351317;
U.S. Patent Application Publication No. 2014/0353373;
U.S. Patent Application Publication No. 2014/0361073;
U.S. Patent Application Publication No. 2014/0361082;
U.S. Patent Application Publication No. 2014/0362184;
U.S. Patent Application Publication No. 2014/0363015;
U.S. Patent Application Publication No. 2014/0369511;
U.S. Patent Application Publication No. 2014/0374483;
U.S. Patent Application Publication No. 2014/0374485;
U.S. Patent Application Publication No. 2015/0001301;
U.S. Patent Application Publication No. 2015/0001304;
U.S. Patent Application Publication No. 2015/0003673;
U.S. Patent Application Publication No. 2015/0009338;
U.S. Patent Application Publication No. 2015/0009610;
U.S. Patent Application Publication No. 2015/0014416;
U.S. Patent Application Publication No. 2015/0021397;
U.S. Patent Application Publication No. 2015/0028102;
U.S. Patent Application Publication No. 2015/0028103;
U.S. Patent Application Publication No. 2015/0028104;
U.S. Patent Application Publication No. 2015/0029002;
U.S. Patent Application Publication No. 2015/0032709;
U.S. Patent Application Publication No. 2015/0039309;

U.S. Patent Application Publication No. 2015/0039878;
U.S. Patent Application Publication No. 2015/0040378;
U.S. Patent Application Publication No. 2015/0048168;
U.S. Patent Application Publication No. 2015/0049347;
U.S. Patent Application Publication No. 2015/0051992;
U.S. Patent Application Publication No. 2015/0053766;
U.S. Patent Application Publication No. 2015/0053768;
U.S. Patent Application Publication No. 2015/0053769;
U.S. Patent Application Publication No. 2015/0060544;
U.S. Patent Application Publication No. 2015/0062366;
U.S. Patent Application Publication No. 2015/0063215;
U.S. Patent Application Publication No. 2015/0063676;
U.S. Patent Application Publication No. 2015/0069130;
U.S. Patent Application Publication No. 2015/0071819;
U.S. Patent Application Publication No. 2015/0083800;
U.S. Patent Application Publication No. 2015/0086114;
U.S. Patent Application Publication No. 2015/0088522;
U.S. Patent Application Publication No. 2015/0096872;
U.S. Patent Application Publication No. 2015/0099557;
U.S. Patent Application Publication No. 2015/0100196;
U.S. Patent Application Publication No. 2015/0102109;
U.S. Patent Application Publication No. 2015/0115035;
U.S. Patent Application Publication No. 2015/0127791;
U.S. Patent Application Publication No. 2015/0128116;
U.S. Patent Application Publication No. 2015/0129659;
U.S. Patent Application Publication No. 2015/0133047;
U.S. Patent Application Publication No. 2015/0134470;
U.S. Patent Application Publication No. 2015/0136851;
U.S. Patent Application Publication No. 2015/0136854;
U.S. Patent Application Publication No. 2015/0142492;
U.S. Patent Application Publication No. 2015/0144692;
U.S. Patent Application Publication No. 2015/0144698;
U.S. Patent Application Publication No. 2015/0144701;
U.S. Patent Application Publication No. 2015/0149946;
U.S. Patent Application Publication No. 2015/0161429;
U.S. Patent Application Publication No. 2015/0169925;
U.S. Patent Application Publication No. 2015/0169929;
U.S. Patent Application Publication No. 2015/0178523;
U.S. Patent Application Publication No. 2015/0178534;
U.S. Patent Application Publication No. 2015/0178535;
U.S. Patent Application Publication No. 2015/0178536;
U.S. Patent Application Publication No. 2015/0178537;
U.S. Patent Application Publication No. 2015/0181093;
U.S. Patent Application Publication No. 2015/0181109;
U.S. patent application Ser. No. 13/367,978 for a Laser Scanning Module Employing an Elastomeric U-Hinge Based Laser Scanning Assembly, filed Feb. 7, 2012 (Feng et al.);
U.S. patent application Ser. No. 29/458,405 for an Electronic Device, filed Jun. 19, 2013 (Fitch et al.);
U.S. patent application Ser. No. 29/459,620 for an Electronic Device Enclosure, filed Jul. 2, 2013 (London et al.);
U.S. patent application Ser. No. 29/468,118 for an Electronic Device Case, filed Sep. 26, 2013 (Oberpriller et al.);
U.S. patent application Ser. No. 14/150,393 for Indicia-reader Having Unitary Construction Scanner, filed Jan. 8, 2014 (Colavito et al.);
U.S. patent application Ser. No. 14/200,405 for Indicia Reader for Size-Limited Applications filed Mar. 7, 2014 (Feng et al.);
U.S. patent application Ser. No. 14/231,898 for Hand-Mounted Indicia-Reading Device with Finger Motion Triggering filed Apr. 1, 2014 (Van Horn et al.);
U.S. patent application Ser. No. 29/486,759 for an Imaging Terminal, filed Apr. 2, 2014 (Oberpriller et al.);
U.S. patent application Ser. No. 14/257,364 for Docking System and Method Using Near Field Communication filed Apr. 21, 2014 (Showering);
U.S. patent application Ser. No. 14/264,173 for Autofocus Lens System for Indicia Readers filed Apr. 29, 2014 (Ackley et al.);
U.S. patent application Ser. No. 14/277,337 for MULTIPURPOSE OPTICAL READER, filed May 14, 2014 (Jovanovski et al.);
U.S. patent application Ser. No. 14/283,282 for TERMINAL HAVING ILLUMINATION AND FOCUS CONTROL filed May 21, 2014 (Liu et al.);
U.S. patent application Ser. No. 14/327,827 for a MOBILE-PHONE ADAPTER FOR ELECTRONIC TRANSACTIONS, filed Jul. 10, 2014 (Hejl);
U.S. patent application Ser. No. 14/334,934 for a SYSTEM AND METHOD FOR INDICIA VERIFICATION, filed Jul. 18, 2014 (Hejl);
U.S. patent application Ser. No. 14/339,708 for LASER SCANNING CODE SYMBOL READING SYSTEM, filed Jul. 24, 2014 (Xian et al.);
U.S. patent application Ser. No. 14/340,627 for an AXIALLY REINFORCED FLEXIBLE SCAN ELEMENT, filed Jul. 25, 2014 (Rueblinger et al.);
U.S. patent application Ser. No. 14/446,391 for MULTIFUNCTION POINT OF SALE APPARATUS WITH OPTICAL SIGNATURE CAPTURE filed Jul. 30, 2014 (Good et al.);
U.S. patent application Ser. No. 14/452,697 for INTERACTIVE INDICIA READER, filed Aug. 6, 2014 (Todeschini);
U.S. patent application Ser. No. 14/453,019 for DIMENSIONING SYSTEM WITH GUIDED ALIGNMENT, filed Aug. 6, 2014 (Li et al.);
U.S. patent application Ser. No. 14/462,801 for MOBILE COMPUTING DEVICE WITH DATA COGNITION SOFTWARE, filed on Aug. 19, 2014 (Todeschini et al.);
U.S. patent application Ser. No. 14/483,056 for VARIABLE DEPTH OF FIELD BARCODE SCANNER filed Sep. 10, 2014 (McCloskey et al.);
U.S. patent application Ser. No. 14/513,808 for IDENTIFYING INVENTORY ITEMS IN A STORAGE FACILITY filed Oct. 14, 2014 (Singel et al.);
U.S. patent application Ser. No. 14/519,195 for HANDHELD DIMENSIONING SYSTEM WITH FEEDBACK filed Oct. 21, 2014 (Laffargue et al.);
U.S. patent application Ser. No. 14/519,179 for DIMENSIONING SYSTEM WITH MULTIPATH INTERFERENCE MITIGATION filed Oct. 21, 2014 (Thuries et al.);
U.S. patent application Ser. No. 14/519,211 for SYSTEM AND METHOD FOR DIMENSIONING filed Oct. 21, 2014 (Ackley et al.);
U.S. patent application Ser. No. 14/519,233 for HANDHELD DIMENSIONER WITH DATA-QUALITY INDICATION filed Oct. 21, 2014 (Laffargue et al.);
U.S. patent application Ser. No. 14/519,249 for HANDHELD DIMENSIONING SYSTEM WITH MEASUREMENT-CONFORMANCE FEEDBACK filed Oct. 21, 2014 (Ackley et al.);
U.S. patent application Ser. No. 14/527,191 for METHOD AND SYSTEM FOR RECOGNIZING SPEECH USING WILDCARDS IN AN EXPECTED RESPONSE filed Oct. 29, 2014 (Braho et al.);
U.S. patent application Ser. No. 14/529,563 for ADAPTABLE INTERFACE FOR A MOBILE COMPUTING DEVICE filed Oct. 31, 2014 (Schoon et al.);

U.S. patent application Ser. No. 14/529,857 for BARCODE READER WITH SECURITY FEATURES filed Oct. 31, 2014 (Todeschini et al.);

U.S. patent application Ser. No. 14/398,542 for PORTABLE ELECTRONIC DEVICES HAVING A SEPARATE LOCATION TRIGGER UNIT FOR USE IN CONTROLLING AN APPLICATION UNIT filed Nov. 3, 2014 (Bian et al.);

U.S. patent application Ser. No. 14/531,154 for DIRECTING AN INSPECTOR THROUGH AN INSPECTION filed Nov. 3, 2014 (Miller et al.);

U.S. patent application Ser. No. 14/533,319 for BARCODE SCANNING SYSTEM USING WEARABLE DEVICE WITH EMBEDDED CAMERA filed Nov. 5, 2014 (Todeschini);

U.S. patent application Ser. No. 14/535,764 for CONCATENATED EXPECTED RESPONSES FOR SPEECH RECOGNITION filed Nov. 7, 2014 (Braho et al.);

U.S. patent application Ser. No. 14/568,305 for AUTO-CONTRAST VIEWFINDER FOR AN INDICIA READER filed Dec. 12, 2014 (Todeschini);

U.S. patent application Ser. No. 14/573,022 for DYNAMIC DIAGNOSTIC INDICATOR GENERATION filed Dec. 17, 2014 (Goldsmith);

U.S. patent application Ser. No. 14/578,627 for SAFETY SYSTEM AND METHOD filed Dec. 22, 2014 (Ackley et al.);

U.S. patent application Ser. No. 14/580,262 for MEDIA GATE FOR THERMAL TRANSFER PRINTERS filed Dec. 23, 2014 (Bowles);

U.S. patent application Ser. No. 14/590,024 for SHELVING AND PACKAGE LOCATING SYSTEMS FOR DELIVERY VEHICLES filed Jan. 6, 2015 (Payne);

U.S. patent application Ser. No. 14/596,757 for SYSTEM AND METHOD FOR DETECTING BARCODE PRINTING ERRORS filed Jan. 14, 2015 (Ackley);

U.S. patent application Ser. No. 14/416,147 for OPTICAL READING APPARATUS HAVING VARIABLE SETTINGS filed Jan. 21, 2015 (Chen et al.);

U.S. patent application Ser. No. 14/614,706 for DEVICE FOR SUPPORTING AN ELECTRONIC TOOL ON A USER'S HAND filed Feb. 5, 2015 (Oberpriller et al.);

U.S. patent application Ser. No. 14/614,796 for CARGO APPORTIONMENT TECHNIQUES filed Feb. 5, 2015 (Morton et al.);

U.S. patent application Ser. No. 29/516,892 for TABLE COMPUTER filed Feb. 6, 2015 (Bidwell et al.);

U.S. patent application Ser. No. 14/619,093 for METHODS FOR TRAINING A SPEECH RECOGNITION SYSTEM filed Feb. 11, 2015 (Pecorari);

U.S. patent application Ser. No. 14/628,708 for DEVICE, SYSTEM, AND METHOD FOR DETERMINING THE STATUS OF CHECKOUT LANES filed Feb. 23, 2015 (Todeschini);

U.S. patent application Ser. No. 14/630,841 for TERMINAL INCLUDING IMAGING ASSEMBLY filed Feb. 25, 2015 (Gomez et al.);

U.S. patent application Ser. No. 14/635,346 for SYSTEM AND METHOD FOR RELIABLE STORE-AND-FORWARD DATA HANDLING BY ENCODED INFORMATION READING TERMINALS filed Mar. 2, 2015 (Sevier);

U.S. patent application Ser. No. 29/519,017 for SCANNER filed Mar. 2, 2015 (Zhou et al.);

U.S. patent application Ser. No. 14/405,278 for DESIGN PATTERN FOR SECURE STORE filed Mar. 9, 2015 (Zhu et al.);

U.S. patent application Ser. No. 14/660,970 for DECODABLE INDICIA READING TERMINAL WITH COMBINED ILLUMINATION filed Mar. 18, 2015 (Kearney et al.);

U.S. patent application Ser. No. 14/661,013 for REPROGRAMMING SYSTEM AND METHOD FOR DEVICES INCLUDING PROGRAMMING SYMBOL filed Mar. 18, 2015 (Soule et al.);

U.S. patent application Ser. No. 14/662,922 for MULTIFUNCTION POINT OF SALE SYSTEM filed Mar. 19, 2015 (Van Horn et al.);

U.S. patent application Ser. No. 14/663,638 for VEHICLE MOUNT COMPUTER WITH CONFIGURABLE IGNITION SWITCH BEHAVIOR filed Mar. 20, 2015 (Davis et al.);

U.S. patent application Ser. No. 14/664,063 for METHOD AND APPLICATION FOR SCANNING A BARCODE WITH A SMART DEVICE WHILE CONTINUOUSLY RUNNING AND DISPLAYING AN APPLICATION ON THE SMART DEVICE DISPLAY filed Mar. 20, 2015 (Todeschini);

U.S. patent application Ser. No. 14/669,280 for TRANSFORMING COMPONENTS OF A WEB PAGE TO VOICE PROMPTS filed Mar. 26, 2015 (Funyak et al.);

U.S. patent application Ser. No. 14/674,329 for AIMER FOR BARCODE SCANNING filed Mar. 31, 2015 (Bidwell);

U.S. patent application Ser. No. 14/676,109 for INDICIA READER filed Apr. 1, 2015 (Huck);

U.S. patent application Ser. No. 14/676,327 for DEVICE MANAGEMENT PROXY FOR SECURE DEVICES filed Apr. 1, 2015 (Yeakley et al.);

U.S. patent application Ser. No. 14/676,898 for NAVIGATION SYSTEM CONFIGURED TO INTEGRATE MOTION SENSING DEVICE INPUTS filed Apr. 2, 2015 (Showering);

U.S. patent application Ser. No. 14/679,275 for DIMENSIONING SYSTEM CALIBRATION SYSTEMS AND METHODS filed Apr. 6, 2015 (Laffargue et al.);

U.S. patent application Ser. No. 29/523,098 for HANDLE FOR A TABLET COMPUTER filed Apr. 7, 2015 (Bidwell et al.);

U.S. patent application Ser. No. 14/682,615 for SYSTEM AND METHOD FOR POWER MANAGEMENT OF MOBILE DEVICES filed Apr. 9, 2015 (Murawski et al.);

U.S. patent application Ser. No. 14/686,822 for MULTIPLE PLATFORM SUPPORT SYSTEM AND METHOD filed Apr. 15, 2015 (Qu et al.);

U.S. patent application Ser. No. 14/687,289 for SYSTEM FOR COMMUNICATION VIA A PERIPHERAL HUB filed Apr. 15, 2015 (Kohtz et al.);

U.S. patent application Ser. No. 29/524,186 for SCANNER filed Apr. 17, 2015 (Zhou et al.);

U.S. patent application Ser. No. 14/695,364 for MEDICATION MANAGEMENT SYSTEM filed Apr. 24, 2015 (Sewell et al.);

U.S. patent application Ser. No. 14/695,923 for SECURE UNATTENDED NETWORK AUTHENTICATION filed Apr. 24, 2015 (Kubler et al.);

U.S. patent application Ser. No. 29/525,068 for TABLET COMPUTER WITH REMOVABLE SCANNING DEVICE filed Apr. 27, 2015 (Schulte et al.);

U.S. patent application Ser. No. 14/699,436 for SYMBOL READING SYSTEM HAVING PREDICTIVE DIAGNOSTICS filed Apr. 29, 2015 (Nahill et al.);

U.S. patent application Ser. No. 14/702,110 for SYSTEM AND METHOD FOR REGULATING BARCODE DATA INJECTION INTO A RUNNING APPLICATION ON A SMART DEVICE filed May 1, 2015 (Todeschini et al.);

U.S. patent application Ser. No. 14/702,979 for TRACKING BATTERY CONDITIONS filed May 4, 2015 (Young et al.);

U.S. patent application Ser. No. 14/704,050 for INTERMEDIATE LINEAR POSITIONING filed May 5, 2015 (Charpentier et al.);

U.S. patent application Ser. No. 14/705,012 for HANDS-FREE HUMAN MACHINE INTERFACE RESPONSIVE TO A DRIVER OF A VEHICLE filed May 6, 2015 (Fitch et al.);

U.S. patent application Ser. No. 14/705,407 for METHOD AND SYSTEM TO PROTECT SOFTWARE-BASED NETWORK-CONNECTED DEVICES FROM ADVANCED PERSISTENT THREAT filed May 6, 2015 (Hussey et al.);

U.S. patent application Ser. No. 14/707,037 for SYSTEM AND METHOD FOR DISPLAY OF INFORMATION USING A VEHICLE-MOUNT COMPUTER filed May 8, 2015 (Chamberlin);

U.S. patent application Ser. No. 14/707,123 for APPLICATION INDEPENDENT DEX/UCS INTERFACE filed May 8, 2015 (Pape);

U.S. patent application Ser. No. 14/707,492 for METHOD AND APPARATUS FOR READING OPTICAL INDICIA USING A PLURALITY OF DATA SOURCES filed May 8, 2015 (Smith et al.);

U.S. patent application Ser. No. 14/710,666 for PRE-PAID USAGE SYSTEM FOR ENCODED INFORMATION READING TERMINALS filed May 13, 2015 (Smith);

U.S. patent application Ser. No. 29/526,918 for CHARGING BASE filed May 14, 2015 (Fitch et al.);

U.S. patent application Ser. No. 14/715,672 for AUGUMENTED REALITY ENABLED HAZARD DISPLAY filed May 19, 2015 (Venkatesha et al.);

U.S. patent application Ser. No. 14/715,916 for EVALUATING IMAGE VALUES filed May 19, 2015 (Ackley);

U.S. patent application Ser. No. 14/722,608 for INTERACTIVE USER INTERFACE FOR CAPTURING A DOCUMENT IN AN IMAGE SIGNAL filed May 27, 2015 (Showering et al.);

U.S. patent application Ser. No. 29/528,165 for IN-COUNTER BARCODE SCANNER filed May 27, 2015 (Oberpriller et al.);

U.S. patent application Ser. No. 14/724,134 for ELECTRONIC DEVICE WITH WIRELESS PATH SELECTION CAPABILITY filed May 28, 2015 (Wang et al.);

U.S. patent application Ser. No. 14/724,849 for METHOD OF PROGRAMMING THE DEFAULT CABLE INTERFACE SOFTWARE IN AN INDICIA READING DEVICE filed May 29, 2015 (Barten);

U.S. patent application Ser. No. 14/724,908 for IMAGING APPARATUS HAVING IMAGING ASSEMBLY filed May 29, 2015 (Barber et al.);

U.S. patent application Ser. No. 14/725,352 for APPARATUS AND METHODS FOR MONITORING ONE OR MORE PORTABLE DATA TERMINALS (Caballero et al.);

U.S. patent application Ser. No. 29/528,590 for ELECTRONIC DEVICE filed May 29, 2015 (Fitch et al.);

U.S. patent application Ser. No. 29/528,890 for MOBILE COMPUTER HOUSING filed Jun. 2, 2015 (Fitch et al.);

U.S. patent application Ser. No. 14/728,397 for DEVICE MANAGEMENT USING VIRTUAL INTERFACES CROSS-REFERENCE TO RELATED APPLICATIONS filed Jun. 2, 2015 (Caballero);

U.S. patent application Ser. No. 14/732,870 for DATA COLLECTION MODULE AND SYSTEM filed Jun. 8, 2015 (Powilleit);

U.S. patent application Ser. No. 29/529,441 for INDICIA READING DEVICE filed Jun. 8, 2015 (Zhou et al.);

U.S. patent application Ser. No. 14/735,717 for INDICIA-READING SYSTEMS HAVING AN INTERFACE WITH A USER'S NERVOUS SYSTEM filed Jun. 10, 2015 (Todeschini);

U.S. patent application Ser. No. 14/738,038 for METHOD OF AND SYSTEM FOR DETECTING OBJECT WEIGHING INTERFERENCES filed Jun. 12, 2015 (Amundsen et al.);

U.S. patent application Ser. No. 14/740,320 for TACTILE SWITCH FOR A MOBILE ELECTRONIC DEVICE filed Jun. 16, 2015 (Bandringa);

U.S. patent application Ser. No. 14/740,373 for CALIBRATING A VOLUME DIMENSIONER filed Jun. 16, 2015 (Ackley et al.);

U.S. patent application Ser. No. 14/742,818 for INDICIA READING SYSTEM EMPLOYING DIGITAL GAIN CONTROL filed Jun. 18, 2015 (Xian et al.);

U.S. patent application Ser. No. 14/743,257 for WIRELESS MESH POINT PORTABLE DATA TERMINAL filed Jun. 18, 2015 (Wang et al.);

U.S. patent application Ser. No. 29/530,600 for CYCLONE filed Jun. 18, 2015 (Vargo et al);

U.S. patent application Ser. No. 14/744,633 for IMAGING APPARATUS COMPRISING IMAGE SENSOR ARRAY HAVING SHARED GLOBAL SHUTTER CIRCUITRY filed Jun. 19, 2015 (Wang);

U.S. patent application Ser. No. 14/744,836 for CLOUD-BASED SYSTEM FOR READING OF DECODABLE INDICIA filed Jun. 19, 2015 (Todeschini et al.);

U.S. patent application Ser. No. 14/745,006 for SELECTIVE OUTPUT OF DECODED MESSAGE DATA filed Jun. 19, 2015 (Todeschini et al.);

U.S. patent application Ser. No. 14/747,197 for OPTICAL PATTERN PROJECTOR filed Jun. 23, 2015 (Thuries et al.);

U.S. patent application Ser. No. 14/747,490 for DUAL-PROJECTOR THREE-DIMENSIONAL SCANNER filed Jun. 23, 2015 (Jovanovski et al.); and U.S. patent application Ser. No. 14/748,446 for CORDLESS INDICIA READER WITH A MULTIFUNCTION COIL FOR WIRELESS CHARGING AND EAS DEACTIVATION, filed Jun. 24, 2015 (Xie et al.).

In the specification and/or figures, typical embodiments of the invention have been disclosed. The present invention is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The invention claimed is:

1. An imaging device for detecting counterfeit bills, the image device comprising:
an objective lens having symmetry around an optical axis, the objective lens configured to disperse images of a bill in longitudinal chromatic aberrations along the optical axis;

a sensor configured to obtain multiple images of the bill, each image corresponding to a specific wavelength within a predetermined spectrum from ultraviolet to near infrared;

a processor configured to analyze the multiple images to detect features of the bill, wherein the processor is configured to process the multiple images to obtain a three-dimensional image stack comprising a plurality of images respectively corresponding to one of a plurality of different wavelengths in the spectrum, wherein the processor is configured to:

compare one or more regions of each of one or more of the plurality of images in the three-dimensional image stack, to one or more regions of a corresponding image of an original bill selected from a three-dimensional image stack comprising a plurality of images of the original bill respectively corresponding to the one of the plurality of different wavelengths in the spectrum; and determine whether the bill is counterfeit based at least in part on the comparison.

2. The imaging device of claim 1, further comprising an electromagnetic radiation source configured to emit broadband spectrum radiation on the bill.

3. The imaging device of claim 2, wherein the electromagnetic radiation source is configured to emit ultraviolet radiation, visible radiation, and near infrared radiation.

4. The imaging device of claim 3, wherein the sensor is configured to sense electromagnetic radiation having wavelengths in the range from about 300 nm to about 1100 nm.

5. The imaging device of claim 1, further comprising a portable housing, wherein the lens and sensor are disposed within the portable housing.

6. The imaging device of claim 5, further comprising barcode scanning components disposed within the portable housing.

7. The imaging device of claim 1, wherein the processor is configured to analyze the multiple images to detect absorption of various wavelengths by the bill.

8. The imaging device of claim 7, wherein the three-dimensional image stack comprises an image corresponding to a wavelength in the visible spectrum, an image corresponding to a wavelength in the ultraviolet spectrum, and an image corresponding to a wavelength in the near infrared spectrum.

9. The imaging device of claim 8, further comprising a memory device configured to store the three-dimensional image stack.

10. The imaging device of claim 1, further comprising a motor configured to move the sensor along the optical axis in a stepwise manner to enable the sensor to obtain the multiple images at each step, each image corresponding to a specific wavelength.

11. The imaging device of claim 1, further comprising a one of a liquid lens and a deformable lens optically aligned with the objective lens, wherein the one of the liquid lens and deformable lens is configured to correct for the longitudinal chromatic aberrations for each image to enable the sensor to obtain the multiple images at a single location.

12. A method for for detecting counterfeit bills, the method comprising the steps of:

optically dispersing multiple wavelengths of light reflected from a bill so as to create longitudinal chromatic aberrations on an optical axis, wherein each wavelength of the light corresponds to a point on the optical axis in a range from ultraviolet to near infrared;

sensing multiple in-focus images of the bill at the multiple wavelengths;

creating a three-dimensional image stack comprising multiple in-focus images corresponding to a plurality of wavelengths in the range;

analyzing one or more of the multiple in-focus images to detect chromatic features of the bill;

comparing the chromatic features corresponding to one or more regions of each of one or more of the multiple in-focus images in the three-dimensional image stack, to one or more regions of a corresponding in-focus images of an original bill selected from a three-dimensional image stack comprising multiple in-focus images of the original bill respectively corresponding to one of the plurality of wavelengths in the range; and determining whether the bill is counterfeit based at least in part on the comparison.

13. The method of claim 12, further comprising the step of disposing an objective lens and a sensor in a handheld device, the objective lens configured for dispersing the images and the sensor configured for sensing the images.

14. The method of claim 13, further comprising the step of moving the sensor along the optical axis to enable the sensor to sense the multiple in-focus images.

15. The method of claim 12, further comprising the step of correcting for the longitudinal chromatic aberrations to enable the sensor to sense the multiple in-focus images at a single location along the optical axis.

16. The method of claim 12, further comprising the step of analyzing the multiple in-focus images to detect absorption of various wavelengths by features of the bill.

17. The method of claim 16, wherein the three-dimensional image stack comprises an image corresponding to a wavelength in the visible spectrum, an image corresponding to a wavelength in the ultraviolet spectrum, and an image corresponding to a wavelength in the near infrared spectrum.

18. The method of claim 12, wherein the multiple wavelengths include at least an ultraviolet wavelength, a visible wavelength, and a near infrared wavelength.

* * * * *